(12) United States Patent
Bochenko et al.

(10) Patent No.: US 8,606,596 B1
(45) Date of Patent: *Dec. 10, 2013

(54) MEDICATION WASTE AND DATA COLLECTION SYSTEM

(75) Inventors: Walter John Bochenko, Encinitas, CA (US); Stephen M. Prince, La Jolla, CA (US); Christopher Biagioli, La Jolla, CA (US); Shawn Wayne DeKalb, San Diego, CA (US)

(73) Assignee: CRISI Medical Systems, Inc., San Diego, CA (US)

( * ) Notice: Subject to any disclaimer, the term of this patent is extended or adjusted under 35 U.S.C. 154(b) by 68 days.

This patent is subject to a terminal disclaimer.

(21) Appl. No.: 13/170,073

(22) Filed: Jun. 27, 2011

Related U.S. Application Data

(60) Provisional application No. 61/358,937, filed on Jun. 27, 2010.

(51) Int. Cl.
   G06Q 10/00 (2012.01)
   G06Q 50/00 (2012.01)

(52) U.S. Cl.
   USPC .......................................................... 705/2

(58) Field of Classification Search
   USPC ........................................................ 705/2, 3
   See application file for complete search history.

(56) References Cited

U.S. PATENT DOCUMENTS

| | | | |
|---|---|---|---|
| 4,650,475 A | 3/1987 | Smith et al. | |
| 4,853,521 A * | 8/1989 | Claeys et al. | ................ 235/375 |
| 4,978,335 A | 12/1990 | Arthur, III | |
| 5,279,576 A | 1/1994 | Loo et al. | |
| 5,628,309 A | 5/1997 | Brown | |
| 5,651,775 A * | 7/1997 | Walker et al. | ................ 604/207 |
| 5,692,640 A | 12/1997 | Caulfield et al. | |
| 5,782,814 A | 7/1998 | Brown et al. | |
| 5,792,117 A | 8/1998 | Brown | |
| 5,873,731 A | 2/1999 | Prendergast | |
| 5,984,901 A | 11/1999 | Sudo et al. | |
| 6,019,745 A | 2/2000 | Gray | |
| 6,123,686 A | 9/2000 | Olsen et al. | |
| 6,338,200 B1 | 1/2002 | Baxa et al. | |
| 6,579,231 B1 | 6/2003 | Phipps | |
| RE38,189 E | 7/2003 | Walker et al. | |
| D481,121 S | 10/2003 | Evans | |
| D485,356 S | 1/2004 | Evans | |
| 6,685,678 B2 | 2/2004 | Evans et al. | |
| 6,790,198 B1 | 9/2004 | White et al. | |
| 6,960,192 B1 | 11/2005 | Flaherty et al. | |
| 7,074,209 B2 | 7/2006 | Evans et al. | |

(Continued)

FOREIGN PATENT DOCUMENTS

DE    29617777 U1    12/1996

OTHER PUBLICATIONS

International Search Report dated Aug. 2, 2011 for corresponding PCT Application No. PCT/US2010/055322.

*Primary Examiner* — Neal Sereboff
*Assistant Examiner* — Jonathan Durant
(74) *Attorney, Agent, or Firm* — Mintz, Levin, Cohn, Ferris, Glovsky and Popeo, P.C.

(57) ABSTRACT

A medication waste and data collection system is provided for use in tracking medication containers, related medication preparation and transfer procedures, medication administration and medication waste disposal. An amount of disposed medication can be reconciled with an amount of medication administered and/or initially prepared. Related apparatus, systems, methods and articles are also described.

23 Claims, 14 Drawing Sheets

(56) References Cited

U.S. PATENT DOCUMENTS

| | | |
|---|---|---|
| 7,115,113 B2 | 10/2006 | Evans et al. |
| 7,117,041 B2 | 10/2006 | Engleson et al. |
| 7,161,488 B2 | 1/2007 | Frasch |
| 7,470,266 B2 | 12/2008 | Massengale et al. |
| 7,722,083 B2 | 5/2010 | McCarthy et al. |
| 7,727,196 B2 | 6/2010 | Neer |
| 7,813,939 B2 | 10/2010 | Clements et al. |
| 7,834,816 B2 | 11/2010 | Marino et al. |
| 7,991,627 B2 | 8/2011 | Hutchinson et al. |
| 8,035,517 B2 | 10/2011 | Gibson |
| 8,151,835 B2 | 4/2012 | Khan et al. |
| 2001/0056258 A1* | 12/2001 | Evans ............... 604/131 |
| 2002/0040208 A1 | 4/2002 | Flaherty et al. |
| 2002/0098598 A1 | 7/2002 | Coffen et al. |
| 2002/0099334 A1* | 7/2002 | Hanson et al. ............ 604/189 |
| 2002/0188259 A1 | 12/2002 | Hickle et al. |
| 2003/0012701 A1 | 1/2003 | Sangha et al. |
| 2003/0052787 A1 | 3/2003 | Zerhusen et al. |
| 2003/0055685 A1 | 3/2003 | Cobb et al. |
| 2003/0065537 A1 | 4/2003 | Evans |
| 2003/0088238 A1 | 5/2003 | Poulsen et al. |
| 2003/0139701 A1 | 7/2003 | White et al. |
| 2003/0140929 A1 | 7/2003 | Wilkes et al. |
| 2003/0174326 A1 | 9/2003 | Rzasa et al. |
| 2004/0051368 A1 | 3/2004 | Caputo et al. |
| 2004/0082918 A1 | 4/2004 | Evans et al. |
| 2004/0186437 A1 | 9/2004 | Frenette et al. |
| 2004/0204673 A1 | 10/2004 | Flaherty |
| 2005/0055242 A1* | 3/2005 | Bello et al. ............... 705/2 |
| 2005/0101905 A1 | 5/2005 | Merry |
| 2005/0106225 A1 | 5/2005 | Massengale et al. |
| 2005/0165559 A1* | 7/2005 | Nelson ............... 702/27 |
| 2005/0182358 A1 | 8/2005 | Veit et al. |
| 2005/0277890 A1 | 12/2005 | Stewart et al. |
| 2006/0079767 A1 | 4/2006 | Gibbs et al. |
| 2006/0079843 A1 | 4/2006 | Brooks et al. |
| 2006/0116639 A1 | 6/2006 | Russell |
| 2006/0122577 A1 | 6/2006 | Poulsen et al. |
| 2006/0144942 A1 | 7/2006 | Evans et al. |
| 2006/0226089 A1 | 10/2006 | Robinson et al. |
| 2006/0229551 A1 | 10/2006 | Martinez et al. |
| 2006/0253346 A1 | 11/2006 | Gomez |
| 2006/0258985 A1 | 11/2006 | Russell |
| 2007/0043335 A1 | 2/2007 | Olsen et al. |
| 2007/0136218 A1 | 6/2007 | Bauer et al. |
| 2007/0166198 A1 | 7/2007 | Sangha et al. |
| 2007/0167919 A1 | 7/2007 | Nemoto et al. |
| 2007/0191787 A1 | 8/2007 | Lim et al. |
| 2007/0279625 A1 | 12/2007 | Rzasa et al. |
| 2007/0299421 A1 | 12/2007 | Gibson |
| 2008/0045930 A1 | 2/2008 | Makin et al. |
| 2008/0051937 A1 | 2/2008 | Khan et al. |
| 2008/0061153 A1 | 3/2008 | Hickle et al. |
| 2008/0125724 A1 | 5/2008 | Monroe |
| 2008/0191013 A1 | 8/2008 | Liberatore |
| 2008/0208042 A1 | 8/2008 | Ortenzi et al. |
| 2008/0234630 A1 | 9/2008 | Iddan et al. |
| 2008/0243088 A1 | 10/2008 | Evans |
| 2008/0294108 A1 | 11/2008 | Briones et al. |
| 2009/0018494 A1 | 1/2009 | Nemoto et al. |
| 2009/0036846 A1 | 2/2009 | Dacquay et al. |
| 2009/0043253 A1 | 2/2009 | Podaima |
| 2009/0069714 A1 | 3/2009 | Eichmann et al. |
| 2009/0149744 A1 | 6/2009 | Nemoto et al. |
| 2009/0157008 A1 | 6/2009 | Vitral |
| 2009/0159654 A1 | 6/2009 | Grimard |
| 2009/0294521 A1 | 12/2009 | de la Huerga |
| 2010/0065643 A1 | 3/2010 | Leyvraz et al. |
| 2010/0152562 A1 | 6/2010 | Goodnow et al. |
| 2010/0153136 A1 | 6/2010 | Whittacre et al. |
| 2010/0174266 A1 | 7/2010 | Estes |
| 2010/0262002 A1 | 10/2010 | Martz |
| 2010/0280486 A1 | 11/2010 | Khair et al. |
| 2010/0305499 A1 | 12/2010 | Matsiev et al. |
| 2011/0060198 A1 | 3/2011 | Bennett et al. |
| 2011/0093279 A1 | 4/2011 | Levine et al. |
| 2011/0111794 A1 | 5/2011 | Bochenko et al. |
| 2011/0112473 A1 | 5/2011 | Bochenko et al. |
| 2011/0112474 A1 | 5/2011 | Bochenko et al. |
| 2011/0152824 A1 | 6/2011 | Diperna et al. |
| 2011/0160655 A1 | 6/2011 | Hanson et al. |
| 2011/0220713 A1 | 9/2011 | Cloninger |
| 2011/0224649 A1 | 9/2011 | Duane et al. |
| 2011/0264069 A1 | 10/2011 | Bochenko |
| 2012/0037266 A1 | 2/2012 | Bochenko |
| 2012/0041355 A1 | 2/2012 | Edman et al. |
| 2012/0222468 A1 | 9/2012 | Nelson et al. |
| 2012/0226446 A1 | 9/2012 | Nelson et al. |
| 2012/0226447 A1 | 9/2012 | Nelson et al. |

* cited by examiner

Sequence of use with an encoded syringe in FIG 6

FIG. 9 Sequence of use with a vial and encoded adapter in FIG 8

Sequence of use with a non-tip-encoded syringe in FIG 10

Examples of RULES for medication alerts, warnings and/or reporting[F]

| Rule | Initial Conditions | Change | | Expected results | | Action?[***] |
|---|---|---|---|---|---|---|
| 1 | Original Volume | minus | Dosed Volume | equals | Wasted Volume | PASS/FAIL? Warning |
| 2 | Original Volume | minus | Wasted Volume | equals | Dosed Volume | PASS/FAIL? Warning |
| 3 | Accessed Container S/N | equals | Patient dosed container S/N | equals | Disposed container S/N | PASS/FAIL? Warning |
| 4[*] | Accessed Container Time | plus "x" | Patient dosed Time | plus "y" | Disposed Volume Time + "x" + "y" | PASS/FAIL? Alert |
| 5 | Accessing Caregiver ID | equals | Patient dosing Caregiver ID | equals | Disposing Caregiver ID | PASS/FAIL? Alert |
| 6[**] | Accessed medication Type | equals | Patient dosed medication Type | equals | Disposed medication Type | PASS/FAIL? Warning |
| 7 | Accessed medication composition and concentration | equals | Wasted medication composition and concentration | equals | Measured medication composition and concentration | PASS/FAIL? Alert |
| 8 | List Access Times/Caregiver | timely within | List Patient dose times/Caregiver | timely within | List Disposals time/Caregiver | Timely and/or Logical? Report |
| 9 | List Med. Types/Caregiver | "x" | List Patient ID/Caregiver | "y" | List Disposals/Caregiver/Witness | Logical? Report |
| 10 | List Access Sequence/Caregiver | Logical? | List Patient Sequence/Caregiver | Logical? | List Disposals Sequence/Caregiver | Logical? Report |
| 11 | List Med. Volumes/Caregiver | Logical? | List Patient Volumes/Caregiver | Logical? | List Disposal Volumes/Caregiver | Logical? Report |

Notes:
* [*] "x" is an allotted time from medication access to patient dosing; "y" is time from patient dosing to time of medication disposal. Times "x" and "y" can be customized for individual institutions (hospitals, EMS agencies, Ambulance agencies, alternate care sites, etc.)

* [**] Medication "type" can be that marked on the container ID Code, that prescribed for and dosed to patient, that verified at waste disposal.

* [***] Alerts, Warnings and/or Reports, can be immediate or periodic. Immediate actions can be to the caregiver and/or caregiver's supervisor. Periodic actons can be hourly, per shift, per day, per week or other time period. Other forms of alerts, warnings and/or reports can be implemented.

* [F] Alerts, Warnings and/or Reports can indicate a potential error in medication (medication diversion or patient dosing). Waste disposal volume greater/less than expected may indicate diversion or patient overdose/underdose.

FIG. 14

MEDICATION WASTE AND DATA COLLECTION SYSTEM

RELATED APPLICATION

This application claims priority to U.S. Pat. App. Ser. No. 61/358,937 filed on Jun. 27, 2010, the contents of which are hereby fully incorporated by reference.

FIELD

The subject matter described herein relates to a medication waste collection apparatus and related data collection systems for use with a wide variety of medication containers.

BACKGROUND

Injectable medications are frequently utilized by healthcare providers (caregivers) in the care of patients in the hospital, in pre-hospital emergency medical services and at alternate care sites (including skilled nursing facilities, home health and hospice settings). Caregivers can include medical doctors, registered nurses, EMS paramedics, dentists and other licensed healthcare practitioners. Accurate documentation of what, when and how much medication is given to a patient is required by healthcare institutions, governmental agencies and regulatory oversight agencies. Many of the medications provided are controlled substances which require additional levels of controlled access, accurate administration documentation and the secure disposal of unused medication and medication containers. Despite the additional access controls provided by automated medication dispensing units on hospital floors, instances of "drug diversion" continue to rise. While most hospitals have automated medication dispensing units on floors to keep drugs locked and near patients who need them, oftentimes, two employees are required to input security IDs to retrieve and log the disposal of various potent drugs and narcotics. However, such security measures may not extend to all areas where the medications are distributed on the floor of a hospital or in the field during emergency medical treatment.

Patient safety and liability issues are increasing the call for pharmaceutical compliance efforts. Hospitals must have procedures in place that include, among other things, validation of a medication's use through patient medical records and a regular review of dispersal records from automated dispensing units against inventory. All narcotic waste is expected to be documented on a Controlled Drug Report by the medication administration nurse and one nurse witness. Although a witness is required for the wastage of controlled substances, the caregiver diverting the medication may choose one of several alternatives and may not get a witness. There may be a request to verify a signature from another nurse without witnessing the actual discard, the diverter may substitute the wasted controlled substance with a clear solution and seek a witness as they discard the clear solution, or document the patient was given an additional dose from the leftover medication. The provider may later request a verifying signature from another provider on the shift with the excuse that they were too busy to get a signature at the time the medication was discarded.

Most drugs are packaged for adults and frequently, patients are administered less that the full amount of drug in a medication container, resulting in unusable drug that becomes waste. Additionally, there is almost always waste in pediatric drug dispensing because most drugs are packaged for adult doses. The process of disposing and documenting controlled substances as waste consumes time and resources. Most practitioners would agree that verifying the dose of a controlled substance prior to administration is a practice standard that should be upheld. But the second part of the verification, verifying remaining medication in a vial, ampoule, bag, syringe or other medication container with residual unused medication to be disposed of as waste is a step identified as cumbersome and easily neglected by practitioners if they are too busy. Disposing of all controlled substances should follow rigorous procedures, not require unnecessary steps for a caregiver and witness to verify actual wastage, be a simple and easy process to follow and include rigorous tracking and reporting procedures.

SUMMARY

In one aspect, a medication waste and data collection system is provided that can include one or more of a data collection system with at least one computing system, a medication injection site, and a waste collection system with an inlet port. The data collection system can receive data from the injection site and/or waste collection system and can determine whether medication within a medication container has been diverted. The medication injection site can characterize administration of medication to a patient and can include a first sensor to generate first data to identify and quantify medication administered to the patient and/or to identify a medication container housing the medication. The waste collection system receives unused medication within the medication container for disposal. The waste collection system can include a second sensor for generating second data to identify and quantify the medication received by the waste collection system and/or to identify the medication container. The medication injection site and the waste collection system can each include a transmitter for wirelessly transmitting the first and second data to the data collection system to allow the determination as to whether the medication has been diverted based on the first and second data. In some cases, the medication injection site can wirelessly transmit data to the waste collection system and/or vice versa (and in such cases the data collection system can be omitted).

The medication waste and data collection system can further include a medication preparation system to characterize the preparation of the medication container prior to administration to the patient. The medication preparation system can generate third data to be communicated to the data collection system so that the data collection system can use this data to further determine whether medication within a medication container has been diverted. The third data can identify the medication container identity, medication and concentration and an amount of medication initially in the medication container and/or identify the medication container. Working together these systems can be separate or inter-connected to provide data and data management services for medication and medication container tracking, timely documentation of patient care activities involving medications, alert messaging services related to medication preparation, medication preparation, medication administration, medication waste disposal and verification of medication waste disposal compliant with healthcare agencies, local, state and/or federal regulations. Medication containers (filled medication containers and/or empty or partially filled medication containers) can be provided with identification codes (ID Codes) enabling the tracking of medications during dispensing, preparation of patient doses and transfer to secondary containers (syringes or other containers) for administration to patients, administration of medications to patients, and the disposal of any unused medication remaining in the dispensed container and/or the prepared secondary container. The medication ID Codes can be positioned at or proximate to the fluid outlet of the medication container such that an ID Code detector located at the fluid inlet of a fluid pathway can identify the ID Code at the point of fluid transfer from one container to another.

In each step of the medication delivery process systems and tracking means can include sensors that generate data to do one or more of the following: identify specific medication containers, identify medication types and/or concentrations, quantify medication preparation and patient administration amounts, identify and quantify medication type and concentration of waste disposal, identify caregivers who perform medication delivery activities, and time stamp (i.e., generate and store a sequence of characters denoting date and/or time to log the events) those medication delivery activities. The data generated by the sensors can be transmitted through wired or wireless communications to data collection systems or to other components within the system for determination of patient care and potential medication diversion.

Medication containers can bear an information element that characterizes the type and concentration of medication contained in the container. The information element can contain information indicative of the identity of the medication container. This information element can be in the form of a barcode, an optical code, an RFID (radio frequency identification device) tag, a magnetic code, a data chip or other data storage media. The information element can be detected by sensors and the data contained in the information element can be provided to a data collection system for tracking, record keeping and diversion detection. The identification element can be disposed proximate to the fluid outlet of the medication container and characterize the identity of the container and/or the contained medication. When the fluid outlet of the container is coupled with the fluid inlet of any of the medication delivery process systems the information contained within the identification element (ID Code) can be detected by sensors and data derived by the sensors can be provided to data collection systems. The data identified in response to a medication container coupling to a fluid inlet of a medication injection site (first data) can be provided to a data collection system. The data identified in response to a medication container coupling to a fluid inlet of a waste collection system (second data) can be provided to a data collection system. The data identified in response to a medication container coupling to a fluid inlet of a medication preparation system (third data) can be provided to a data collection system. Each of these three data elements can include data from a volume measurement sensor within the system.

Data can be detected and transmitted to data collection systems at any and all of medication delivery process steps including but not limited to: medication container dispensing at a dispensing station, a medication preparation using a preparation system, a medication administration to a patient through a medication injection system, a medication disposal into a waste collection system. Data received by the data collection system can be processed through a set of rules to determine potential medication diversion. Reports and/or messages to supervisors and administrative personnel can be generated based on the rule-set data processing providing information for control and tracking of medications, the documentation of caregiver medication delivery activity and patient medication administration records. The rule-set can be applied to the data and can provide an expected medication amount (volume) visible or invisible to the caregiver at the point of medication administration for verification of complete medication administration to the patient and/or at the point of medication disposal a visual indication to caregivers and witnessing personnel of the expected disposal of unused medication amounts. Alert messages can be generated based on a comparison of expected and actual medication amounts indicating complete or incomplete medication delivery to a patient.

In a second aspect, a fluid handling system is provided for receiving a medication container having a fluid outlet and for reporting information to a data collection system. The fluid handling system can include a medication injection site including a fluid inlet configured to receive the fluid outlet of the medication container, a sensor configured to read identifying information from the medication container, a sensor configured to generate injected volume information indicative of an amount of medication injected into the medication site and a transmitter configured to transmit the identifying and injected volume information to the data collection system. The fluid handling system can also include a liquid waste injection site. The liquid waste injection site can include a fluid inlet configured to receive the fluid outlet of a medication container, a sensor configured to read the identifying information, a sensor configured to generate disposed volume information indicative of an amount of medication injected into the waste injection site and a transmitter configured to transmit the identifying and disposed volume information to the data collection system. The fluid handling system can also include a medication preparation apparatus. The medication preparation apparatus can include a fluid coupler configured to transfer medication from a vial or a syringe to a medication container, a sensor configured to read the identifying information, a sensor configured to generate transferred volume information indicative of an amount transferred to the medication container and a transmitter configured to transmit the identifying and transferred volume information to the data collection system.

In a third aspect, a liquid waste injection site is provided for receiving a medication container having a fluid outlet and reporting information to a data collection system. The liquid injection site can include a waste containment reservoir, a fluid inlet coupled to the waste containment reservoir and configured to receive the fluid outlet, a sensor configured to read identifying information from the medication container in response to the fluid inlet being coupled to the fluid outlet, a sensor configured to measure a volume of fluid transferred from the mediation container to the waste containment reservoir and a transmitter configured to wirelessly transmit the information indicative of the identifying information and the volume of fluid to the data collection system.

In a fourth aspect, a system is provided comprising a tamper-proof or tamper evident housing, a fluid inlet accessible on an outer surface of the housing, a liquid waste reservoir disposed within the housing, a detection element disposed within the housing and a data collection system to store data. The fluid inlet can be configured to receive a fluid outlet of a medication container. The medication container can have at least one identification element characterizing the identity and/or medication contained within the medication container. The liquid waste reservoir can be coupled to the fluid inlet to receive medication from the medication container when expelled through the fluid inlet. The detection element can be configured to automatically detect the at least one identification element when the medication container is coupled to the fluid inlet. The data collection system can store data characterizing the medication container identity and the amount of medication transferred to the waste reservoir.

In a fifth aspect, a system is provided comprising a tamper-proof or tamper evident housing, a fluid inlet accessible on an outer surface of the housing, a liquid waste container disposed within the housing, a volume element disposed within the housing and a data collection system to store data characterizing the medication container identity and/or volume of medication transferred to the waste reservoir. The fluid inlet can be configured to receive a fluid outlet of a medication container. The liquid waste container can be coupled to the fluid inlet to receive medication from the medication container when expelled through the fluid inlet. The volume element can be configured to automatically determine a volume of medication expelled from the medication container via the fluid inlet. The data collection system can be configured to reconcile an amount transferred to the waste reservoir with an amount initially contained within the medication container.

In a sixth aspect, system is provided comprising at least one data collection system comprising at least one computing system, a plurality of medication injection sites, a plurality of waste collection systems and wherein the at least one data collection system determines whether medication within the medication container has been diverted based on the received first and second data. The at least one data collection system can include at least one computing system. Each medication injection site can be configured to provide data characterizing administration of medication to a patient and comprising at least one first sensor to generate first data to identify and quantify medication administered to the patient and to identify a medication container housing the medication. Each medication injection site can transmit data generated by the at least one first sensor to the at least one data collection system. Each waste collection system can be configured to receive unused medication within the medication containers for disposal. Each waste collection system can include at least one second sensor to generate second data to identify and quantify medication received by the at least one waste collection system and to identify medication containers housing the medication. Each waste collection system can be configured to transmit a second data from the at least one second sensor to the at least one data collection system. The at least one data collection system can be configured to determine whether medication within the medication container has been diverted based on the received first and second data.

The system can also include a plurality of medication preparation systems to each prepare medication containers prior to administration of the medication to the patient such that the at least one data collection system further determines whether medication within the medication container has been diverted based on the third data. The plurality of medication preparation systems can each generate third data identifying the medication and an amount of medication initially in the medication container and can be in communication with the at least one data collection system. The system can further be configured to determine whether medication within the medication container has been diverted based on the third data. The system can include a first sensor that generates the first data in response to the medication container being coupled to a corresponding medication injection site. The system can include a second sensor that generates the second data in response to the medication container being coupled to a corresponding waste collection system.

In a yet another aspect, a medication waste and data collection system is provided that can include a tamper proof (or tamper evident) waste container housing, an injection site, a liquid waste container, a solid waste container, a data communication transmission element, a data collection system and a medication container with residual unused medication requiring disposal. Medication containers can take many forms and include, but are not limited to syringes, vials, ampoules, bags, pre-filled pouches and cartridges, rigid containers and flexible containers. The intelligent injection site includes, a fluid inlet to receive a fluid outlet of a used, partially used or refused medication container, a detection element to receive medication identification information (ID Code) from the medication container, a volume element to measure the medication waste volume and a transmission element to communicate information to a data collection system. The intelligent injection site can contain a clock for time stamping information, a memory element to store information prior to transmission to the data collection system and a processor to precondition sensor information and/or calculate values, apply rules, manage messages and alerts, and control data entry, indicators and data flow. Data collected can be transmitted by a transmission element through a direct wired connection or wirelessly.

The waste container housing can be stand-alone, associated with and part of a sharp's container and/or other medical waste system, or wholly contained as a sub-system of a more comprehensive medical waste management system. The waste container can be associated with a medication dispensing station. The housing can be tamper-proof (or tamper-evident) and provide for one-way waste access only to the caregiver disposing the medications. Access can be through a fluid inlet on the outer surface for receiving the fluid outlet of a medication container, through data entry of caregiver identification, access to medication ID code scanning means and access to solid waste container deposit chamber. Access for emptying the liquid and/or solid waste containers can be restricted to authorized operators only with a key (physical key, ID code data entry key, an electronic key or other restricted access method keys). The waste container housing can be tamper proof or tamper evident and rigidly affixed to a solid surface such as a wall, a floor, an emergency vehicle, a piece of furniture (medication inventory control station or cabinet, caregiver workstation, medical waste management system, patient care workstation, storage cabinet, or other fixed installation healthcare facility equipment) to limit medication diversion and/or access to any of the waste contents.

Disposed within the housing can be an injection site with a detection element to manually or automatically detect the ID code of the medication container, a volume element to automatically determine the volume of the expelled medication, a verifier element to automatically determine a composition of the medication being expelled from the medication container, a liquid waste container to receive the expelled medication, a solid waste container to receive non-liquid controlled substances and medication containers after the medication has been expelled, a data collection memory element to time-stamp and log medication disposals and a transmission element to communicate data characterizing the waste disposal activities to a data collection system for record keeping and reporting.

Within the waste container housing a liquid waste container is fluidically connected to the intelligent injection site to receive residual unused medication for disposal. The liquid waste container can contain a disinfecting or neutralizing agent like bleach to render the wasted medication unusable and bio-safe. The transmission element can be hardwired or wireless and can immediately transmit or store in memory information about the medication waste for use by a data collection system. The data collection system can include a processor, clock and memory to record medication waste information in a time stamped history file for reconciliation with dose volumes administered to patients. Verification of proper and/or improper medication waste disposal based on a rule set can be reported to cellular phones, medical devices such as a smart IV pump that includes a software application, electronic medical records (EMR), medical information systems (MIS) and pharmacy information systems (PIS) for institutional compliance, discrepancy detection, tracking and reporting. The text and figures herein describe a mix of elements forming a closed-loop medication diversion control system.

In a yet another aspect, the medication waste collection apparatus and data collection system can be provided with a personnel identification subsystem to positively identify the person (or persons) disposing of the unused medication and associate that identity with the medication administered or wasted. The personnel identification ID entry means can be any one of a swiped magnetic strip identification card, a proximity detected identification card, an ID number and password entry, an optical image, a symbolic pattern, a biometric recognition such as a fingerprint, a retinal scan, etc. The personnel identification subsystem can also include an entry of a reference to a specific patient that was treated with the medication container.

In a yet another aspect, the medication waste collection apparatus and data collection system can be provided with a solid waste container. The solid waste container can provide for waste disposal of used medication containers that have been emptied. The solid waste container can contain a disinfecting/neutralizing agent like bleach to render the solid waste unusable and bio-safe.

Primary medication containers (containers originating from a pharmaceutical manufacturer, pharmacy re-packager or pharmacy associated with a healthcare facility can contain medication ID code source information that describes the manufacturer, medication container identity, medication type, concentration, dose, container size and dosage form. The medication identification code source can be any one or more of a unique code, a one dimensional barcode, a two dimensional barcode, an optical image, an NDC code (National Drug Code), a segment of the NDC code identifying the drug product, a segment of the NDC code identifying the drug package, a unique identifier code, human readable code, a machine readable code, a manually entered code or other codes that can be created to uniquely identify one or more of a medication's manufacturer, re-packager, distributer, strength (concentration), dosage form, formulation, package form, package size, contained volume, dose, container serial number, lot number, expiration date. The primary medication container can be used to administer medication to a patient. In this case, the primary medication container ID code can be read or detected by an intelligent injection site connected to a patient. The ID code identifier can be at the fluid outlet of the primary container thus enabling an intelligent injection site to identify the ID code at a fluid inlet.

In a further variation, a medication preparation and transfer apparatus can contain one or more medication container ID code identifiers that when used can identify a primary medication container ID code and a secondary medication container ID code. These ID codes can be associated with one another at the point of fluid transfer. The ID code identifiers can be at the fluid outlet of the containers thus enabling a medication transfer apparatus or patient injection site to detect and identify the ID code at a fluid inlet. The transfer apparatus can be used for the transfer of medication from vials, ampoules, bags, syringes or other rigid or flexible medication containers to secondary medication containers (bags, syringes or other rigid or flexible medication containers) for patient administration. Here, the primary medication container identification ID code can transfer to (or be associated with in a data collection system) the secondary medication container when the medication is transferred from the primary container to the secondary container. The secondary medication container can include a unique ID code that identifies an individual secondary container. The secondary medication container can then be used to deliver the medication to the patient. When connected to the patient's injection site, the secondary medication container ID code can be read by a detection element and information transferred to a data collection system.

The detection element of the intelligent injection site can be any one of a an optical detector, a bar-code reader, a unique code reader, a magnetic strip reader, a proximity reader, an optical image capture device like a camera, a manual data input information string detector, a stored alpha numeric character string detector, a unique symbolic identifier detector, a mechanical identifier detector, an RFID detector, a data chip reader.

The medication container or medication transfer apparatus with encoded information source can be selected from a group comprising: optically encoded information, optical image information, magnetically encoded information, capacitively coupled encoded information, radio frequency detectable information, RFID tag information, electronic data chip information and mechanically detectable information.

The volume element of the intelligent injection site can be any one of a pressure sensor, differential pressure sensor, flow sensor, thermal time-of-flight sensor, thermal plume sensor, vibration sensor, acoustic sensor, ultrasonic sensor, paddle wheel sensor, optical volume/displacement measurement sensor, an optical turbulent flow IR sensing flow/volume sensor, coriolis sensor, turbine sensor, nutating disk volume sensor. Alternately, the volume element can be a liquid waste volume monitor. The liquid waste volume monitor can detect initial liquid waste amounts contained in the liquid waste container. The liquid waste volume monitor can be a liquid level detector, a strain gage weight detector, an ultrasonic liquid waste level detector, a float level detector and any one of a number of other liquid level detectors. Here, the initial condition would indicate no liquid waste. Then as medication containers are attached and residual medication is disposed of the level indicator can indicate volumes disposed of for each medication container attached. Similar to weight based scales, a "tare" value (original value−new value) can indicate the disposed volume. This disposed volume is transmitted to the data collection system for reconciliation.

The waste container housing can include visual and/or audio indicators providing feedback to the user that the user ID information has been properly entered, the unused residual medication has been disposed of and that the wasted medication transaction has been properly recorded. Other indicators can include user feedback on one or more of: proper ID entry, recognition of the medication container identification code, verification that medication has previously been dispensed, volume measurement of the disposed medication, medication type and concentration verification indicator, transmission of data to a data collection system, alert messages or indications on improper operation of the medication waste collection apparatus and data collection system, completion of solid waste disposal, a liquid waste level indicator, need to empty a full liquid waste container, need to empty a full solid waste container.

Additionally, an indicator can be provided such as a "reconciliation error warning" that gives immediate feedback to the caregiver and/or witness that the wasted medication indicates a possible diversion. The reconciliation error can be any one of an incorrect injected volume, an incorrect medication type, an incorrect medication concentration, an incorrect medication container ID code, an incorrect user ID entry. Error indicators can be any one of an audible tone, a visual indicator, a visual message, an electronic mail message, A reconciliation error warning message can be provided to any of the EMR/MIS/PIS systems, a medical device such as a smart IV pump, a message (in audio or text form) to a cellular phone, a message to a land-line phone, a message to a computer system at a central caregiver station of a hospital, EMS station, or alternate care site.

In a yet another aspect, the medication waste collection apparatus and data collection system can be provided with a set of rules to provide supervisors real-time information about the medication waste disposal process. Rules can be programmable to customize procedures for individual healthcare organization procedures (SOP's) and alerts, warnings and reports generated based on these rules. Rules can be any number of but not limited to the following: a time limit between acquisition of medication and administration of medication, a time limit between administration of medication and residual waste disposal, a time limit between the scheduled (ordered) medication administration time and actual administration time, a difference in the original medication container volume and patient injected volume, a difference in medication concentration between the primary medication container concentration and the residual fluid disposed of concentration, the expected residual volume and actual disposed of volume, the expected caregiver ID and actual caregiver ID, the original medication container serial number acquired for patient dosing, the serial number or unique ID code of the secondary medication container used for patient dose administration and the actual medication container serial number or unique ID code used for medication waste disposal, atypical waste amounts for a caregiver compared to his or her peers, aberrant activity by caregivers flagged for surveillance through other means, the location of patient dose administration and the location of medication waste disposal, a combination of the above rules, a combination of the above rules with other rules.

The liquid waste container can be a flexible bag or a rigid bottle with tubing connecting it to the intelligent injection site. The waste container housing along with the intelligent injection site can be manufactured complete as a disposable device with a self contained power source or can be constructed with reusable portions with a replaceable disposable liquid waste container, replaceable solid waste container and a rechargeable battery or AC power connected power source.

The liquid waste container can include a tracking element. The tracking element can be utilized to identify the waste contents as hazardous, non-hazardous, information regarding the dates, times, volumes, concentrations and/or medication types disposed of in the liquid waste container. The liquid waste container tracking element can be serialized for tracking of proper waste disposal when the liquid waste container is removed from the waste collection housing. The waste container housing can include a waste container data transfer element. The waste container data transfer element can transfer tracking information from the liquid waste collection apparatus to the tracking element on the liquid waste container. The waste container tracking element can be an RFID tag, an data chip, a magnetic strip or other data storage media with encoded information.

The data collection system can be connected to an electronic medical records database. The medical waste collection apparatus, data collection system or the electronic medical records database can provide software algorithms and rules to reconcile original medication container volumes with original medication container access time, patient medication injection volumes and times, and the time and unused medication waste volume injected (disposed) into the liquid waste container. The reconciliation process can identify unresolved waste exceptions and provide reports, warnings and alerts for follow-up.

In yet another variation of the medication waste collection apparatus and data collection system, an ID code reader can be included to read medication container ID codes. This ID code information can be used by the waste management system to identify the medication container in-place of the encoded container ID Code provided at the fluid outlet. The code reader can be any one of a conventional one dimensional bar code reader, a 2-dimensional bar code reader, etc. Alternately, the ID code reader can be replaced with an RFID reader, a magnetic strip reader, an electronic chip reader, an optical image reader, a proximity code reader, etc. to function as a medication container identification element.

In another variation of the medication waste collection apparatus and data collection system, a transaction record can be included to provide the caregiver a receipt of the medication disposal. This record can be provided in addition to the data collection system record. This receipt can be in the form of a printed receipt, and electronic receipt, a simple transaction data card (magnetic or other) that is produced or updated when the medication disposal operation is completed. This receipt can be used as an alternative to or in addition to a visual or audible indication and can be retained by the caregiver for security, proof of waste activity and/or safety purposes.

In yet another variation of the medication waste collection apparatus and data collection system, a medication verification sub-system can be included to verify the type and concentration of fluid disposed. The medication verification sub-system can include a sensor or plurality of sensors that determines if the fluid being disposed is the same medication and concentration indicated by the medication ID Code. The sensor can be any one or more of a pH detector, a viscosity indicator, an optical density indicator, a chemical indicator, a drug molecule indicator, a drug sensor, a spectroscopic sensor, a spectrophotometer, an HPLC detector, a UV detector, a fluid density sensor, a specific gravity fluid sensor, etc.

In yet another variation of the medication waste collection apparatus and data collection system, the housing can include a drain for the disposal of liquid waste. The drain can connect directly to the liquid waste container and allow removal and proper disposal of the waste medication. Alternately, the waste container can be removable from the housing entirely and a drain connected for disposal of the liquid waste. In other implementations, the liquid waste container can be completely disposable and not include a drain connection.

In yet another variation, multiple medication waste container housings can be installed in any number of patient care rooms, or EMS vehicles in a fleet, each with a transmission capability to a centralized master data collection system. In this variation, unused residual medication can be disposed of immediately in a housing next to the patient and data logged locally and/or sent to a centralized location for reconciliation. An alternate to this configuration can be a fleet of EMS vehicles each with its own medication waste collection apparatus. Here an EMS central station can receive transmissions from waste disposal collection system regarding atypical waste amounts for a caregiver compared to his or her peers, aberrant activity by caregivers flagged for surveillance through other means, each vehicle, reconcile waste volumes and times and provide alerts, warnings and reports. Accurate and timely reconciliation at the end of caregiver (EMS based, hospital based, non-hospital based and/or alternate care site based workers) work shifts can be facilitated. Any number of alternate configurations can be embodied to fit a fixed or mobile healthcare system.

A system can also be provided that includes a medication injection site to automatically characterize medication administered to a patient from a medication container, a waste collection system to receive unused medication within the medication container and to automatically characterize the received unused medication, and a data collection system receiving data from each of the medication injection site and the waste collection system to determine whether medication has been diverted subsequent to the administration of medication to the patient. In such an arrangement one or both of the medication injection site and the waste collection system can use a composition sensor (e.g., a spectroscopic sensor, etc.) to characterize a composition of the medication. The composition sensor can generate signatures of the medication passing therethrough which can be compared to known signatures in order to characterize the medication.

The subject matter described herein provides many advantages for identification of medication containers, tracking and accounting of medication preparation, medication administration and/or residual medication waste disposal. These advantages provide a more comprehensive system improving the control and reporting of medication administration and waste disposal; particularly for controlled or hazardous substances. For example hospitals and emergency medical services can provide localized intelligent and automated medication waste disposal housings distributed throughout patient care areas thus improving the ease and accuracy of medication administration and waste disposal. Automated data tracking of medication containers, medication dose preparation activity, medication administration to patients and residual medication waste disposal can provide incentives to caregivers to properly dispose of medication waste while providing accurate tracking and reporting capabilities for organizations to identify potential drug diversion personnel or scenarios. Standard operating procedure (SOP) rules and reporting systems can be more easily followed by caregivers and caregiver supervisors with less effort thus freeing up time for patient care.

The details of one or more variations of the subject matter described herein are set forth in the accompanying drawings and the description below. Other features and advantages of the subject matter described herein will be apparent from the description and drawings, and from the claims.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed embodiments. In the drawings:

FIGS. 4 and 4A are diagrams illustrating a second alternate medication waste collection apparatus and data collection system as in FIG. 2;

FIGS. 10 and 10A are diagrams illustrating the sequence of use of a medication waste and data collection system as in FIG. 4;

FIG. 14 is a table illustrating possible medication waste disposal rules.

Like reference symbols in the various drawings indicate like or similar elements.

DETAILED DESCRIPTION

Figure 1:
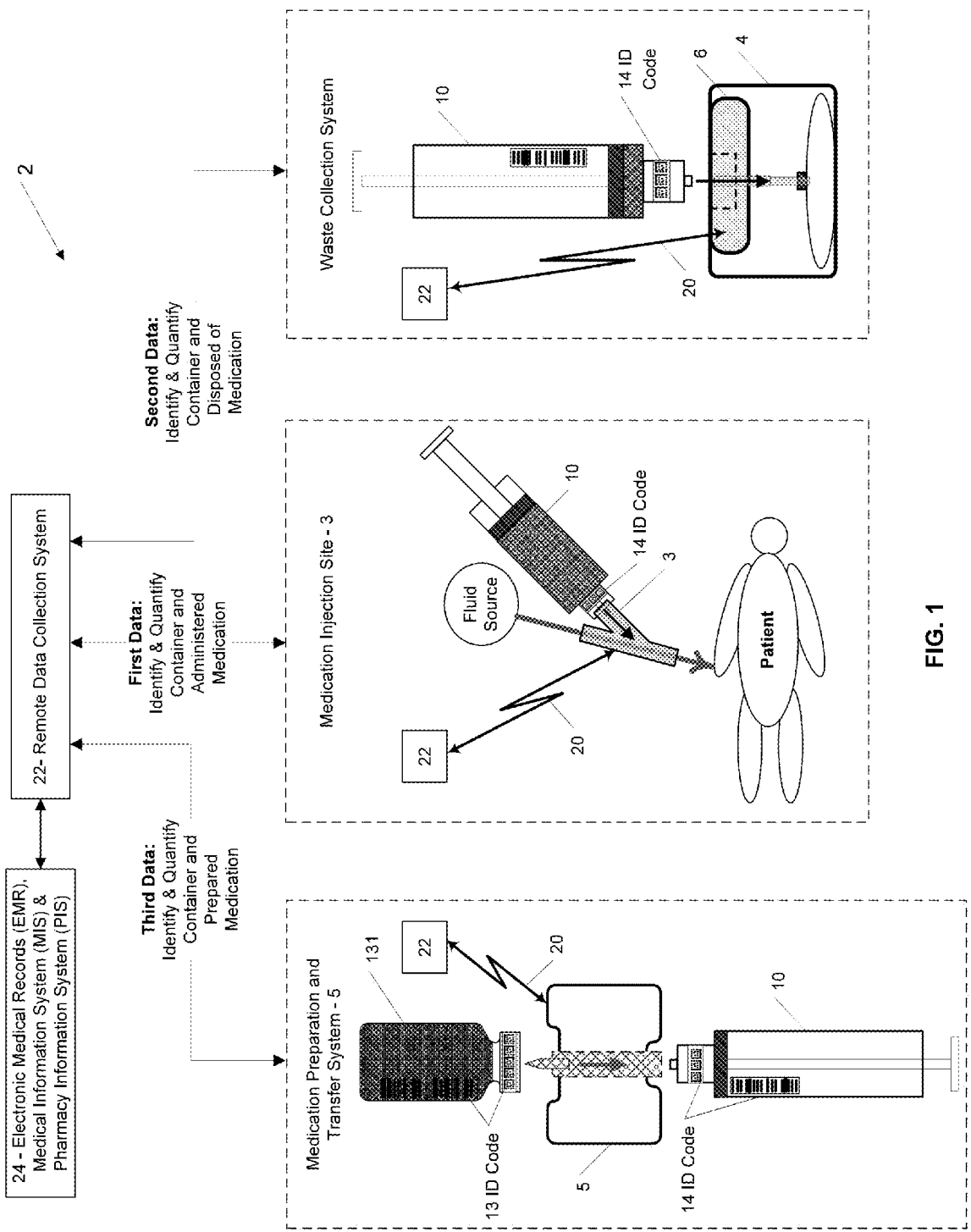
FIG. 1 is a diagram illustrating a medication waste and data collection system.

FIG. 1 is a diagram illustrating a medication waste and data collection system 2. System 2 can include an intelligent medication injection site 3 for administration of medications to patients, a waste collection system with an intelligent injection site 6 for identifying medication containers with waste, and a medication preparation and transfer system 5 for identifying primary and/or secondary medication containers during the preparation of medications. The medication injection site 3 can be connected to fluid delivery administration tubing and a fluid source. Injection site 3 can identify ID Code 14 on medication container 10 and provide first tracking data to (remote) data collection system 22. The data collection system 22 is referred to as "remote" because it can be physically separated from the preparation and transfer system 5, the injection site 3, and the waste container 4 thus requiring wireless 20 or wired data transmissions between the data collection system and other sites (3, 4, and 5). The waste collection system's intelligent injection site can identify ID Code 14 on medication container 10 and provide second tracking data to remote data collection system 22. The medication preparation and transfer system 5 can identify ID Code 13 on medication container 131 (prefilled vial or syringe), identify ID Code 14 on secondary container 10 and provide third data to remote data collection system 22. First, second and/or third data can be provided to remote data collection system 22 by wired or wireless transmissions 20.

Remote data collection system 22 can include rules, algorithms, messaging and/or recordkeeping processes and memory for maintaining a history of activity within the system. Data collection system 22 can provide and/or receive rules, algorithms and other information from system 24 for the systematic accounting of medications dispensed, prepared, transferred, administered and/or disposed of (wasted). First, second and third data provided to remote data collection system 22 can provide tracking data specific to medication containers (ID codes) facilitating accurate and timely medication records documentation.

The medication injection site 3, intelligent injection site 6 and/or medication preparation and transfer system 5 can operate and/or utilize encoded medication containers in a similar manner to that described and illustrated in co-pending applications: U.S. patent application Ser. No. 12/614,276, entitled "MEDICATION INJECTION SITE AND DATA COLLECTION SYSTEM" filed on Nov. 6, 2009, U.S. patent application Ser. No. 12/765,707, entitled "MEDICATION INJECTION SITE AND DATA COLLECTION SYSTEM" filed on Apr. 22, 2010 and U.S. patent application Ser. No. 12/938,300, entitled "MEDICATION INJECTION SITE AND DATA COLLECTION SYSTEM" filed on Nov. 2, 2010. In addition, various aspects of preparing medication containers with encoded identification information and the detection of such information is described and illustrated in co-pending U.S. patent application Ser. No. 12/768,509, entitled "MEDICATION AND IDENTIFICATION INFORMATION TRANSFER APPARATUS" filed on Apr. 27, 2010 and U.S. provisional Pat. App. Ser. No. 61/497,855, entitled "MEDICATION DOSE PREPARATION AND TRANSFER SYSTEM" filed on Jun. 16, 2011. The contents of each of the applications described above are hereby fully incorporated by reference.

Figure 2:
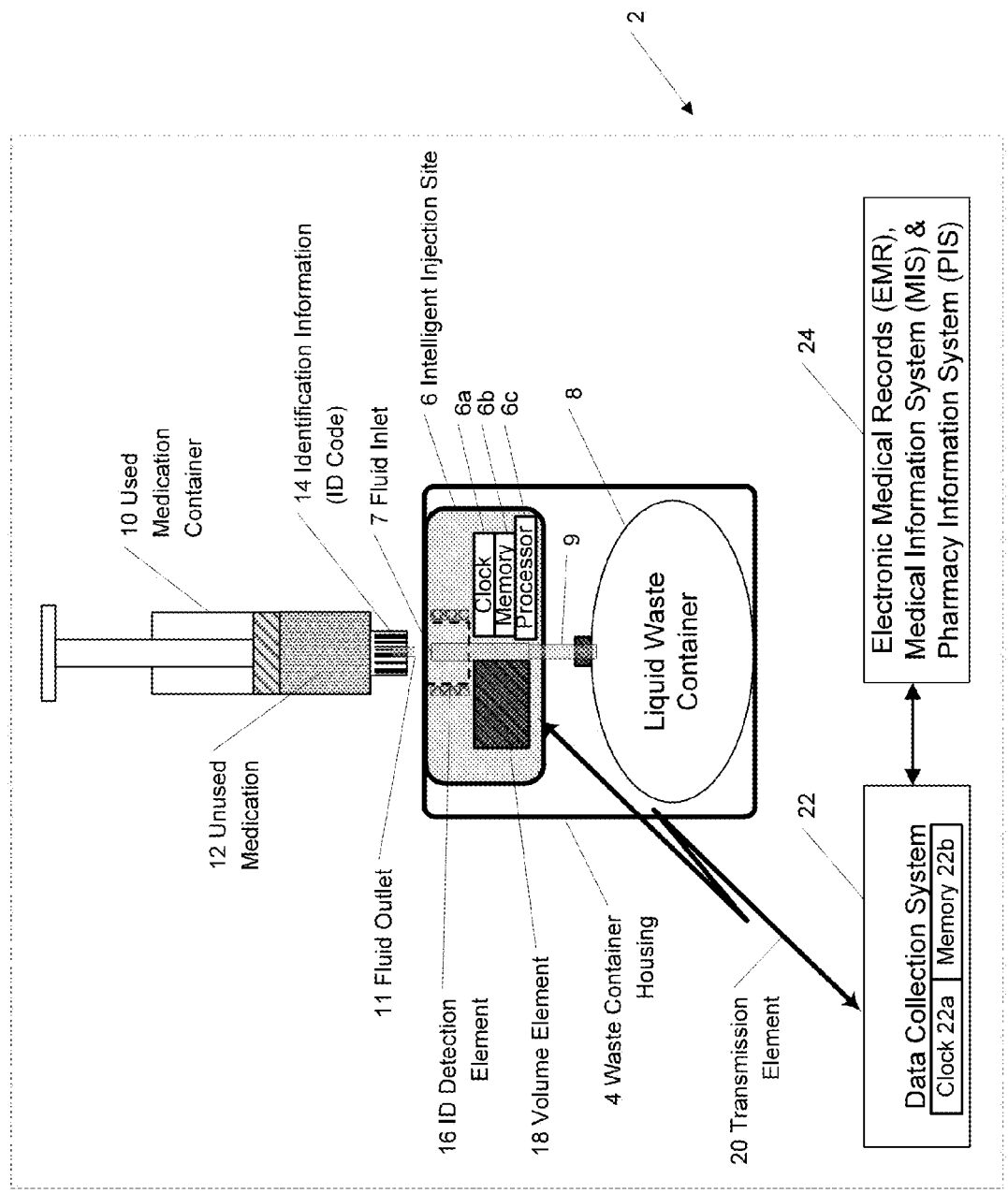
FIG. 2 is a detailed diagram illustrating a medication waste and data collection system.

FIG. 2 is a detailed diagram illustrating a medication waste collection apparatus and data collection system 2. System 2 can include waste container housing 4 that can include intelligent injection site 6, liquid waste container 8 configured to receive residual medication 12 from the used medication container 10 through the fluid inlet 7, a fluid conduit 9, medication container 10, data collection system 22 and electronic medical records (EMR), medical information system (MIS) and pharmacy information system (PIS) 24. Intelligent injection site 6 can include a fluid inlet 7 configured to receive a fluid outlet 11 of an unused, used, partially used or refused medication container 10, an ID detection element 16 to detect identification code source 14 located at the fluid outlet 11 of medication container 10, a volume element 18 to measure the volume of unused medication 12 that is disposed of into waste container 8, a clock 6a to time stamp recorded events, memory 6b to store a log of events and processor 6c to calculate and process data. Fluid conduit 9 can connect intelligent injection site 6 to liquid waste container 8 for the transfer of liquid from injection site 6 to liquid waste container 8. Intelligent injection site 6 can include a transmission element 20 to communicate information to data collection system 22. The data (information) transfer element 20 can be configured to transfer information from the medication container 10 to an information data collection system 22 that is indicative of the residual medication that has been transferred from the used medication container to the liquid waste container 8. Data transmission element 20 can be one of: hardwired transmission, wireless transmission, IR transmission, optical transmission, electromagnetically coupled transmission. The data collection system 22 can include a real time clock 22a and memory 22b to time stamp and log transmissions from intelligent injection site 6. Electronic medical records (EMR), medical information system (MIS) and pharmacy information system (PIS) 24 can receive information from data collection system 22 for distribution to clinical professionals in the form of alerts, reports, and summaries about drug reconciliation and potential medication diversion issues. In addition, electronic medical records (EMR), medical information systems (MIS) and pharmacy information systems (PIS) 24 can provide information to data collection system 22 to facilitate the reconciliation of medication delivery and waste disposal. Here the total volume of medication provided in the original medication container must equal the sum of the volume injected into the patient and the volume disposed of into the liquid waste container. Differences may indicate drug diversion and form a basis for an alert, warning and/or corrective action. The waste disposal step can be before medication administration to a patient (dispose of medication not intended for patient administration first, then administer residual to a patient) or dispose step can be after medication administration to a patient (administer medication to a patient first, then dispose of any residual unused medication).

As depicted in FIG. 2 the waste collection apparatus and system 2 may include two different types of sensors including a sensor 16 configured to read identifying information 14 and a sensor 18 configured to measure a fluid transfer from the medication container 10 to the waste container 8. The sensor 16 is the same as or similar to an equivalent sensor used by the injection site 3 to read the same identifying information 14. The sensor 18 is the same or similar to an equivalent sensor used by injection site 3 to measure a fluid transfer from the medication container 8 to the injection site 3 and to the patient. Utilizing similar sensors for injection and disposal simplifies the process of identifying and measuring the use and disposal of container 8.

Figure 3:
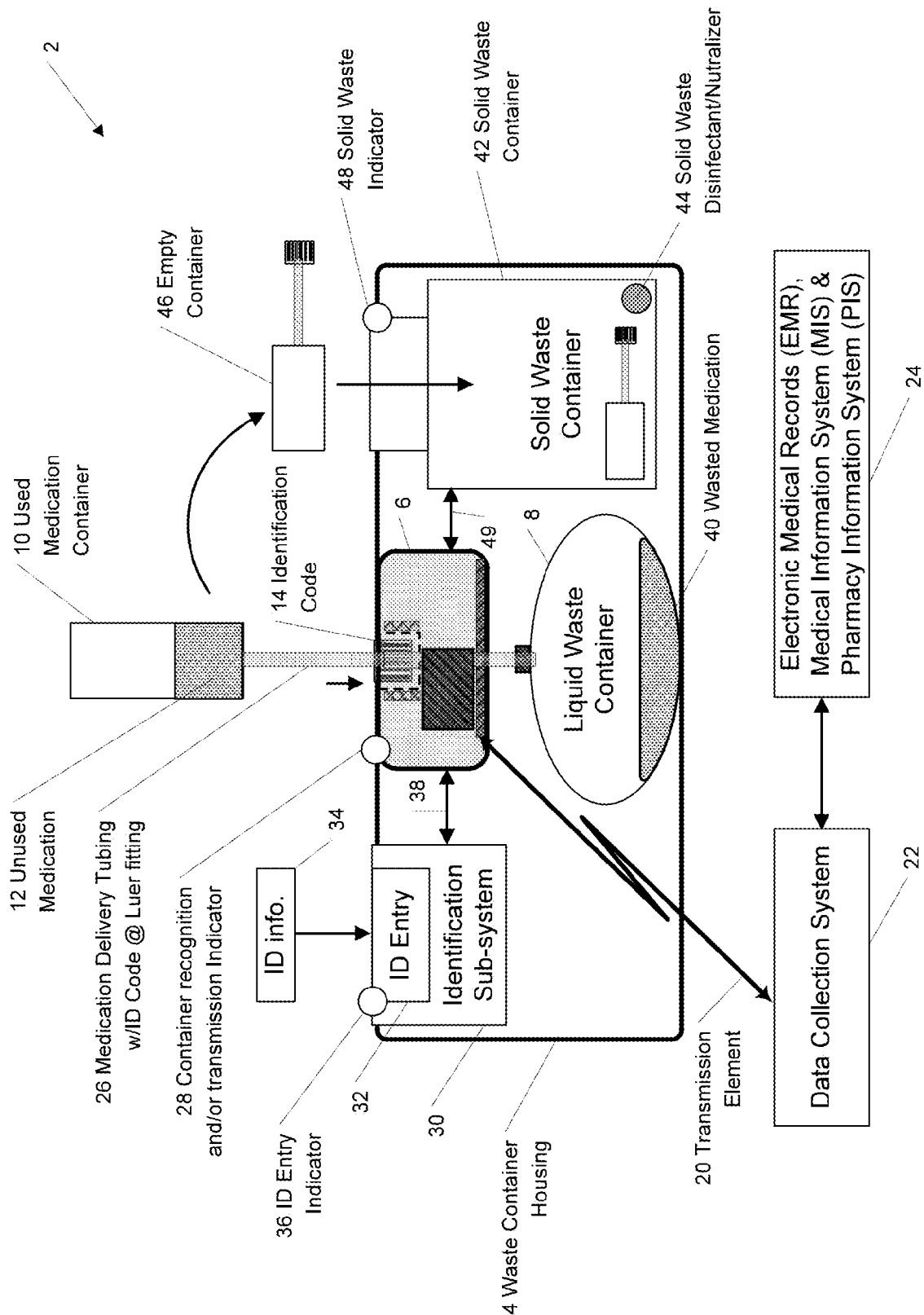
FIG. 3 is a diagram illustrating an alternate medication waste collection apparatus and data collection system as in FIG. 2.

FIG. 3 is an alternate medication waste collection apparatus and data collection system that includes a personnel identification sub-system 30 and can include a solid waste container 42. In this variation medication container 10 with fluid medication is different from the syringe shown in FIG. 2 and can be a flexible bag, a rigid or semi-rigid container, a single or multi-compartment container, a vial with a fluid outlet, an elastomeric container, a flat pack pouch and many other containers. Medication container 10 can include attached tubing 26 with a luer fitting for attachment to intelligent injection site 6. The luer fitting forms the fluid outlet and can include identification code 14. Unused medication 12 is delivered to the fluid inlet of intelligent injection site 6 for disposal. When the luer fitting fluid outlet on delivery tubing 26 is engaged with intelligent injection site 6 fluid inlet, container recognition indicator 28 can confirm proper attachment. Indicator 28 can be an LED, an LCD, an alphanumeric display, or other any one of a number of other visual and/or audio indicators, printers and display technologies.

In use, identification sub-system 30 can include a user ID entry element 32 to facilitate entry of ID information 34 forming a record of who is disposing of unused medication 12 and an ID entry indicator 36 to indicate entry success. ID entry 32 can be a keypad for manual entry, a bar-code reader, a magnetic strip swipe reader, a proximity reader, an optical reader, a biometric reader (fingerprint, retinal scan, biomarker). ID information 34 can include a personal identification code and password. The identification sub-system can be used by multiple users to provide human verification of waste disposal. Once ID information 34 is entered it can be passed onto intelligent injection site 6 through element 38 for transmission 20 to data collection system 22 or time stamped and stored locally in memory 6b for later transmission (refer to FIG. 2). ID entry indicator 36 can be an LED, an LCD, an alphanumeric display, or other any one of a number of other visual indicators.

A second aspect of the medication waste collection apparatus and data collection system shown in FIG. 3 can include a solid waste container 42 for the disposal of non-liquid medications (pills, patches, topical ointments) in empty container 46. After medication container 10 is attached to intelligent injection port 6 and residual unused medication 12 is expelled from medication container 10, it is transported to liquid waste container 8 as wasted medication 40. Solid waste container 42 can receive and store one or more non-liquid medications and empty containers 46. Solid waste container 42 can contain a disinfectant-neutralizer element 44 to render any residual medication waste within the medication container 10 unusable and bio-safe. Solid waste disinfectant-neutralizer 44 can be a disinfecting or neutralizing agent like bleach to render the wasted medication unusable and bio-safe. When empty container 46 is put into solid waste container 42 signal 49 and solid waste indicator 48 are activated to indicate solid waste disposal. Signal 49 can be communicated to data collection system 22 by transmission element 20 to record the event.

Figure 4:
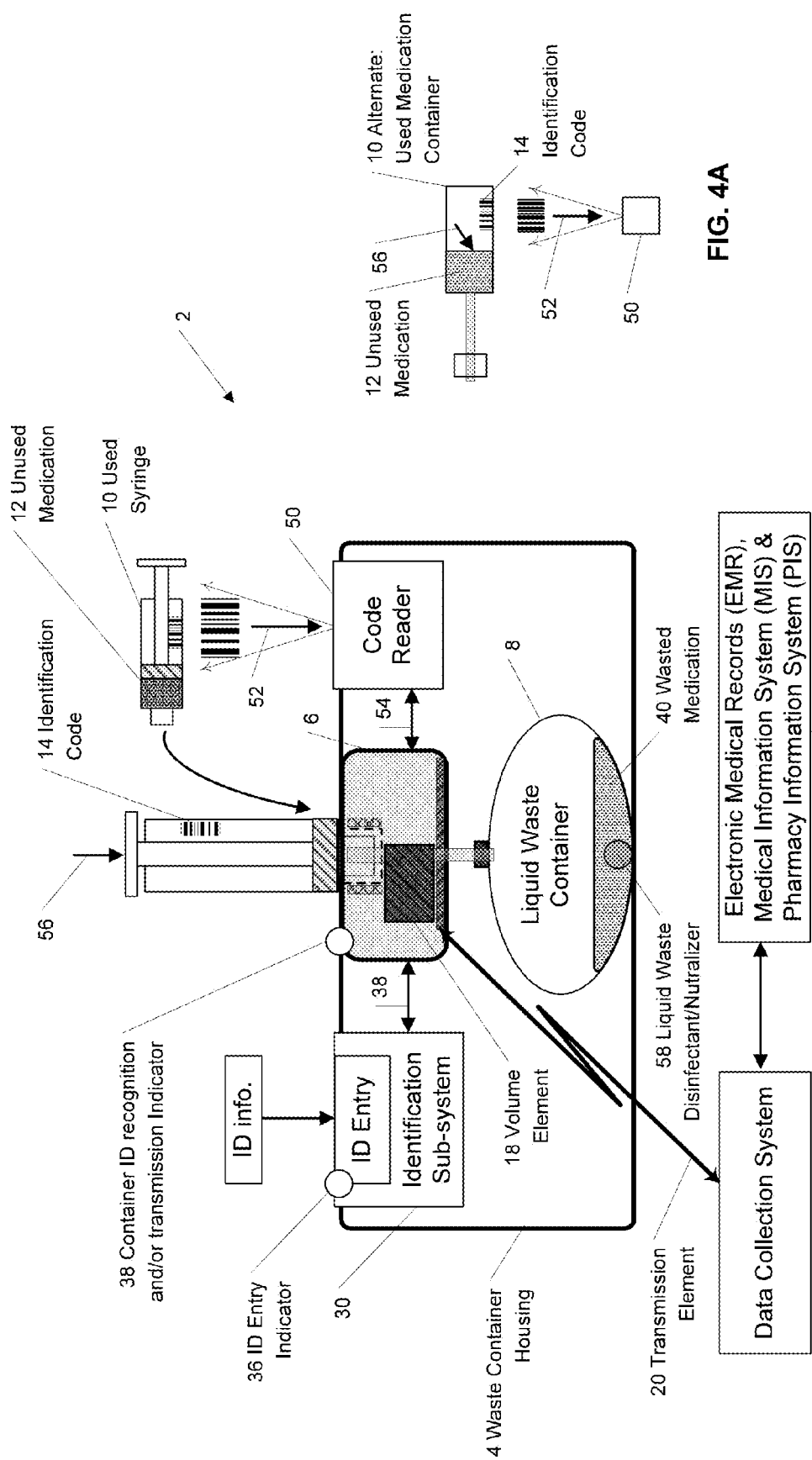

FIG. 4 is a second alternate medication waste collection apparatus and data collection system that includes a code reader 50. Code reader 50 can include a one dimensional barcode reader, a two dimensional barcode reader, an RFID reader, an electronic data chip reader, a magnetic strip code reader or other unique code optical reader. In this variation medication container 10 is different from the syringe as shown in FIG. 2 in that the identification code 14 is located elsewhere on the container than the fluid outlet (such as on the body of the container). The identification code 14 can be a unique ID code identifying the individual primary medication container or individual secondary medication container.

Shown to the right in FIG. 4A a non-syringe medication container can also have identification code 14. Code reader 50 can scan medication container 10 to access identification code 14. The coded data 52 can then be transferred to intelligent injection site 6 through connection 54. Similar to FIG. 2, the identification code can then be transmitted to data collection system 22 by transmission element 20. After medication container 10 is scanned, it can be attached to intelligent injection site 6 for medication waste disposal. A force element 56 can be applied to container 10 causing unused medication 12 to be displaced into the waste collection apparatus. Volume element 18 can measure the volume of unused medication 12 that is disposed of into waste container 8. Clock 6a (or 22a) can time stamp events and memory 6b (or 22b) can store a log of events (not shown, refer to FIG. 2).

A second aspect of the medication waste collection apparatus and data collection system 2 shown in FIG. 4 can include a liquid waste disinfectant/neutralizer 58 contained in liquid waste container 8 for the purpose of disinfecting the liquid waste, making it unusable and/or rendering it bio-safe. Disinfecting or neutralizing agent 58 can be solid or liquid bleach, Lysol® brand disinfectant other similar disinfecting agents.

Figure 5:
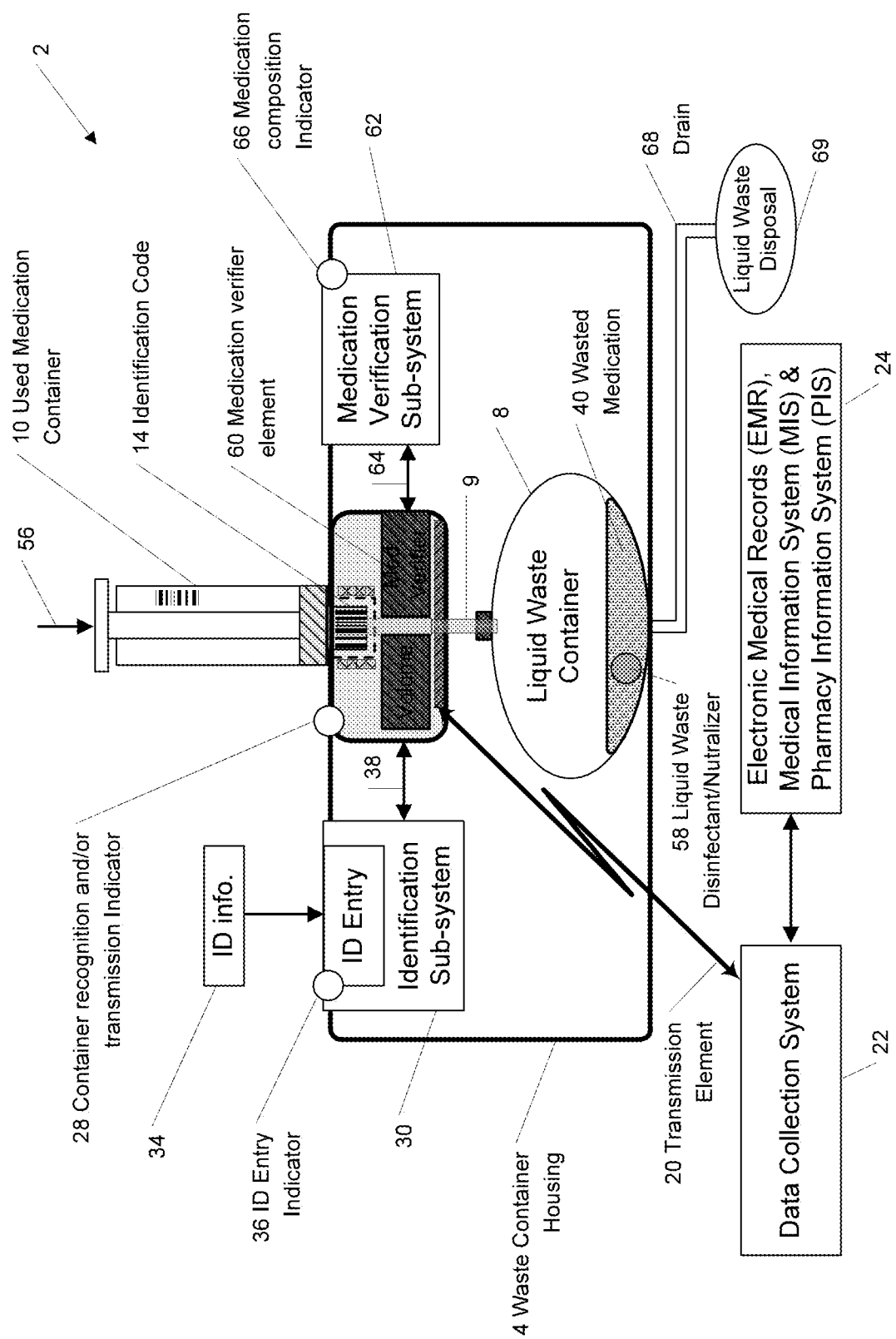
FIG. 5 is a diagram illustrating a third alternate medication waste collection apparatus and data collection system as in FIG. 2.

FIG. 5 is a diagram illustrating a third alternate medication waste collection apparatus and data collection system as in FIG. 2 that can include a medication verification sub-system 62. A medication verification sub-system 62 can provide a verification that the fluid injected into the liquid waste container 8 is the same as the medication expected and indicated by identification code 14 on medication container 10. The medication verification sub-system 62 can contain a medication verifier element 60 that senses the properties of the injected fluid to determine its composition. Verifier element 60 can be any one or more of a pH detector, a viscosity indicator, an optical density indicator, a chemical indicator, a drug molecule indicator, a drug sensor, a spectroscopic sensor, a spectrophotometer, an HPLC detector, a UV detector, a fluid density sensor, a specific gravity sensor, etc. Alternately, or in combination with the above, the medication verifier element 60 can be a combination of a number of measured parameters, including but not limited to the above parameters, that populate a table with values indicative of the medication. The table can be included in medication verification sub-system 62, intelligent injection site 6 or data collection system 22. The table can be compared to a stored look-up table with a known set of parameter values for a specific medication type and concentration to determine the actual medication type and/or concentration of the fluid disposed. In this variation when unused medication 12 is injected into the medication waste collection apparatus medication passes through fluid conduit 9 where verifier element 60 can detect the type and/or concentration of medication injected.

Information from verifier element 60 can communicate (link 64) with medication verification sub-system 62 to classify the medication type and concentration and subsequently provide an indication of the medication type and concentration 66 to the user. Medication type and concentration information is transmitted to data collection system 22 by transmission element 20. If a mis-match of expected medication type or concentration to actual medication type or concentration is determined, data collection system 22 can invoke an alert to the user and/or notify electronic medical records, medical information system and pharmacy information system 24 (EMR/MIS/PIS 24) of such a mis-match. Appropriate follow-up reporting can be included in either data collection system 22 or EMR/MIS/PIS 24.

A second aspect of the medication waste collection apparatus and data collection system shown in FIG. 5 can include a drain 68 for removal and disposal of wasted medication 40. Drain 68 can empty liquid waste container 8 of wasted medication 40 and transfer it to a liquid waste disposal container 69 for ultimate disposal. Liquid waste container 8 can provide for easy replacement of liquid waste disinfectant/neutralizer 58 thus reconditioning the system for future use. The liquid waste container 8 can include an input port (not shown) for adding a liquid waste disinfectant/neutralizer 58. The liquid waste container 8 can include a liquid waste level detector element and level detection indicator to detect and inform the user of the need to replace the liquid waste container which will be discussed later in FIG. 13.

Figure 6:
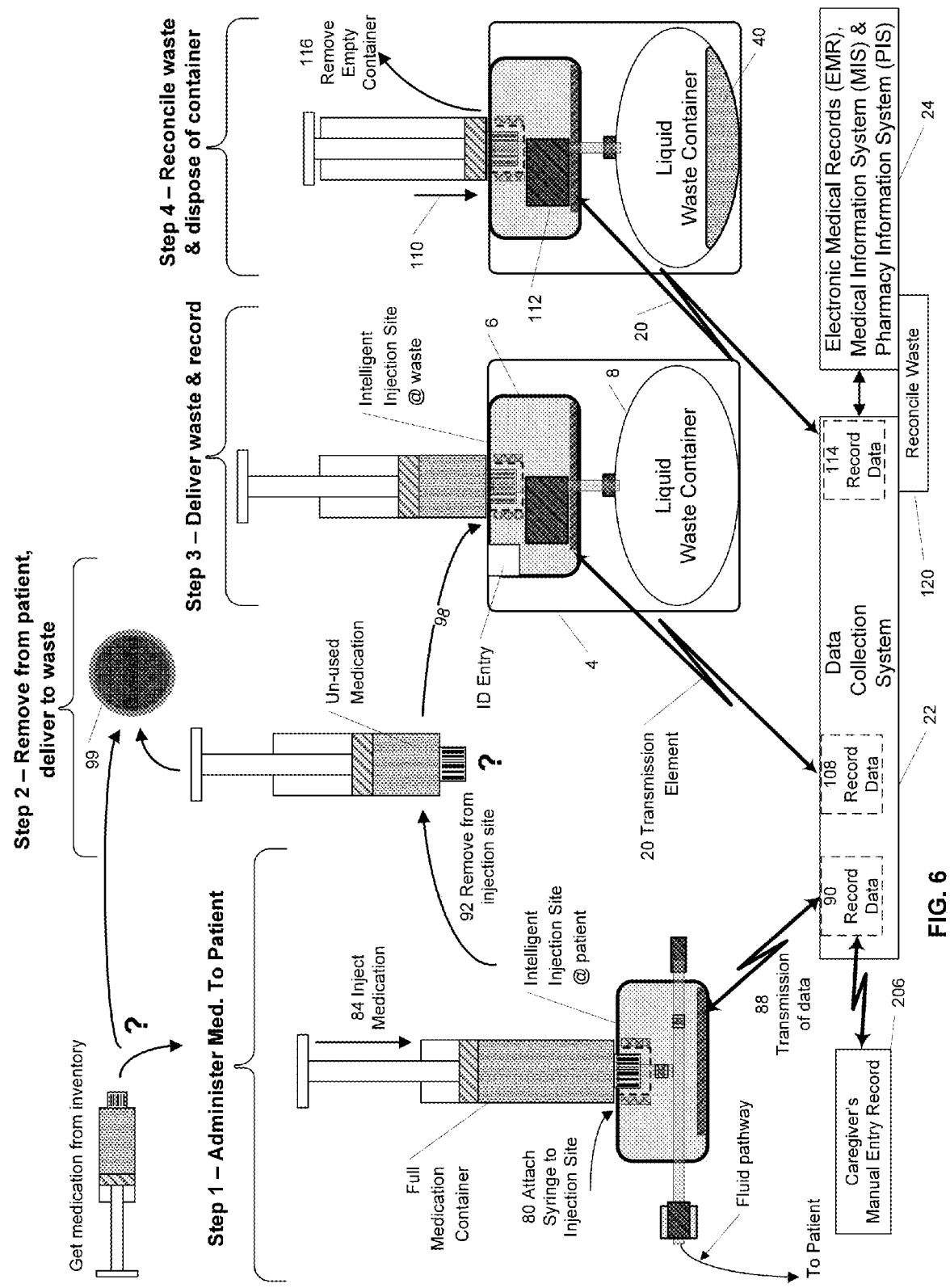
FIG. 6 is a diagram illustrating a sequence of use of a medication waste and data collection system as in FIG. 2 with a syringe.
Figure 7:
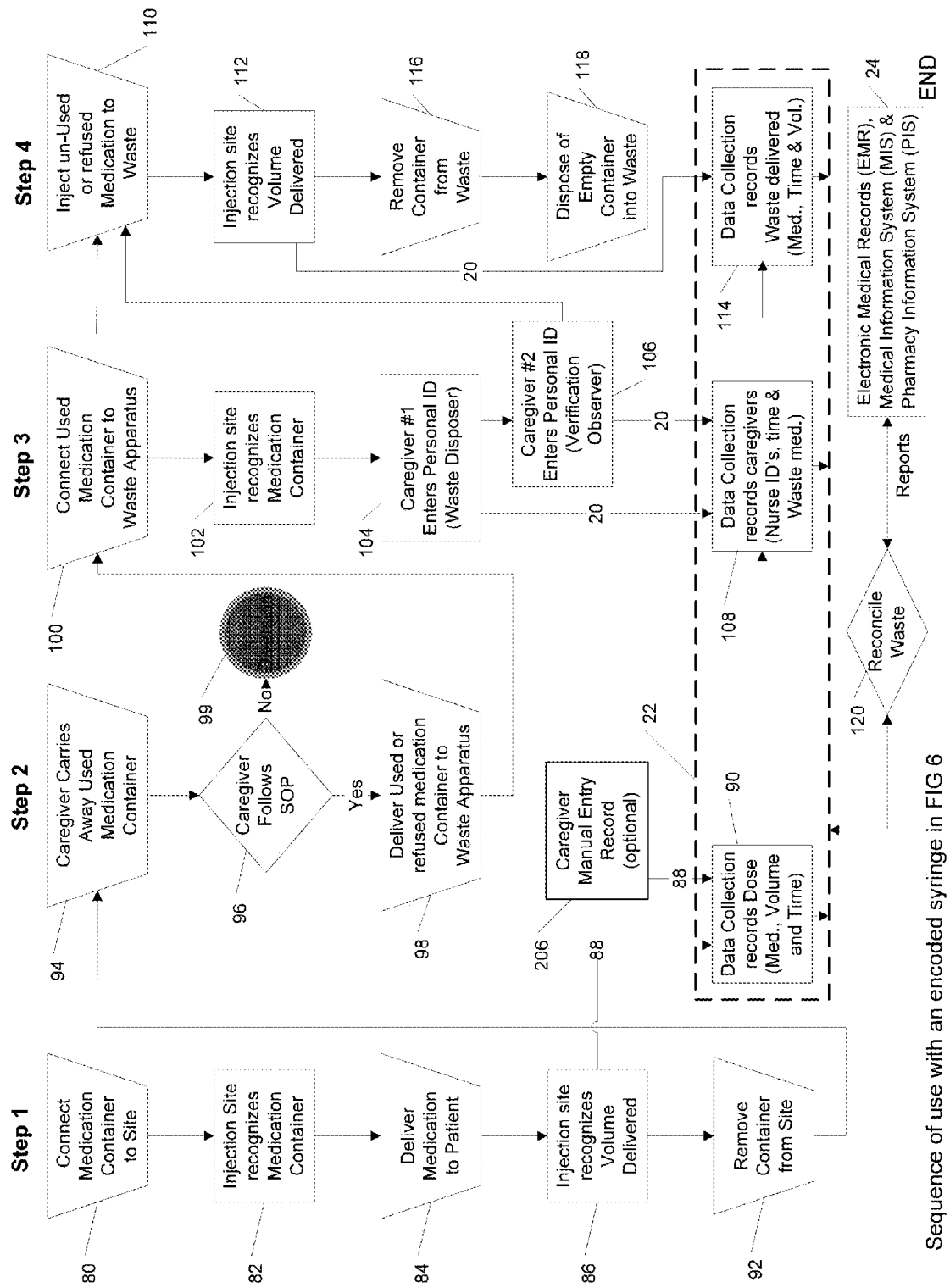
FIG. 7 is a logic flow diagram illustrating the process steps of FIG. 6.

FIGS. 6 and 7 are diagrams illustrating a sequence of use of a medication waste and data collection system 2 as in FIG. 2 with a syringe. There are 4 major steps in the process:

Step 1—Get medication from inventory. Administer medication dose to patient;

Step 2—Remove used container from patient's injection site and deliver any unused medication to waste disposal system;

Step 3—Deliver unused medication to a liquid waste collection apparatus and record waste disposal.

Step 4—Reconcile waste and dispose of empty container.

The following example is a more detailed description of the process and moves from left to right. Numbers in parentheses (#) refer to sub-steps as shown in FIGS. 6 and 7. There may be any number of sequences in the administration of medications to patients and the recording of data for these steps. Each sequence would typically follow the basic steps of acquiring medication, administering medication, and disposing of unused medication. Alternately, the unused medication portion can be disposed of first and then the remaining dose of medication administered to the patient.

Step 1—Medication is prescribed and a full medication container is accessed from inventory for patient care. A caregiver (usually a nurse, but can be any healthcare provider including an emergency services caregiver) attaches medication container to an intelligent injection site connected to a patient (80). The intelligent injection site recognizes the medication container identification code (82). The caregiver injects the medication (84) which is delivered to the patient via a fluid pathway. The volume of medication delivered is measured by the intelligent injection site (86) and first data

(88) is time stamped and temporarily stored or immediately transmitted to data collection system 22 where medication container identity, medication type, concentration, volume and time is recorded (90). Alternately, data record 90 can be received from a caregiver manual entry record 206 or a transcription of a paper record (not shown). The caregiver then removes the container from the injection site (92) and leaves the patient.

Step 2—Caregiver carries away medication container (94) and decides how to dispose of unused medication according to standard operating procedures (SOP) (96). If caregiver diverts medication (99), SOP is not followed. If caregiver follows SOP, unused medication is delivered to a medication waste collection apparatus (98).

Step 3—Caregiver locates the waste disposal apparatus and connects medication container 10 to intelligent injection site 6 at waste apparatus (100). Injection site 6 recognizes the medication container ID code (102). Caregiver #1 enters personal ID information into waste disposal system (104). Caregiver #2 enters personal ID information into waste disposal system (106). Medication container ID Code and Caregivers' ID information (second data) is transmitted (20) to data collection system 22 where information is recorded (108).

Step 4—Caregiver #1 (or #2) disposes of unused medication by injecting medication into injection site (110). Caregiver #2 (or #1) observes disposal process and injection site recognizes the wasted medication volume (112) and transmits 20 (second data) medication ID Code 14, volume injected and time data to data collection system 22. Data collection system 22 records data (114). Medication container is removed from waste system (116) and empty container is disposed of in solid waste (118). Data collection 22 (or EMR/MIS/PIS 24) reconciles waste volume (120) using original medication container volume from ID Code minus volume injected into patient (90) with wasted medication volume (114) and credits Caregiver #1 and Caregiver #2 with proper medication disposal (reports).

Figure 8:
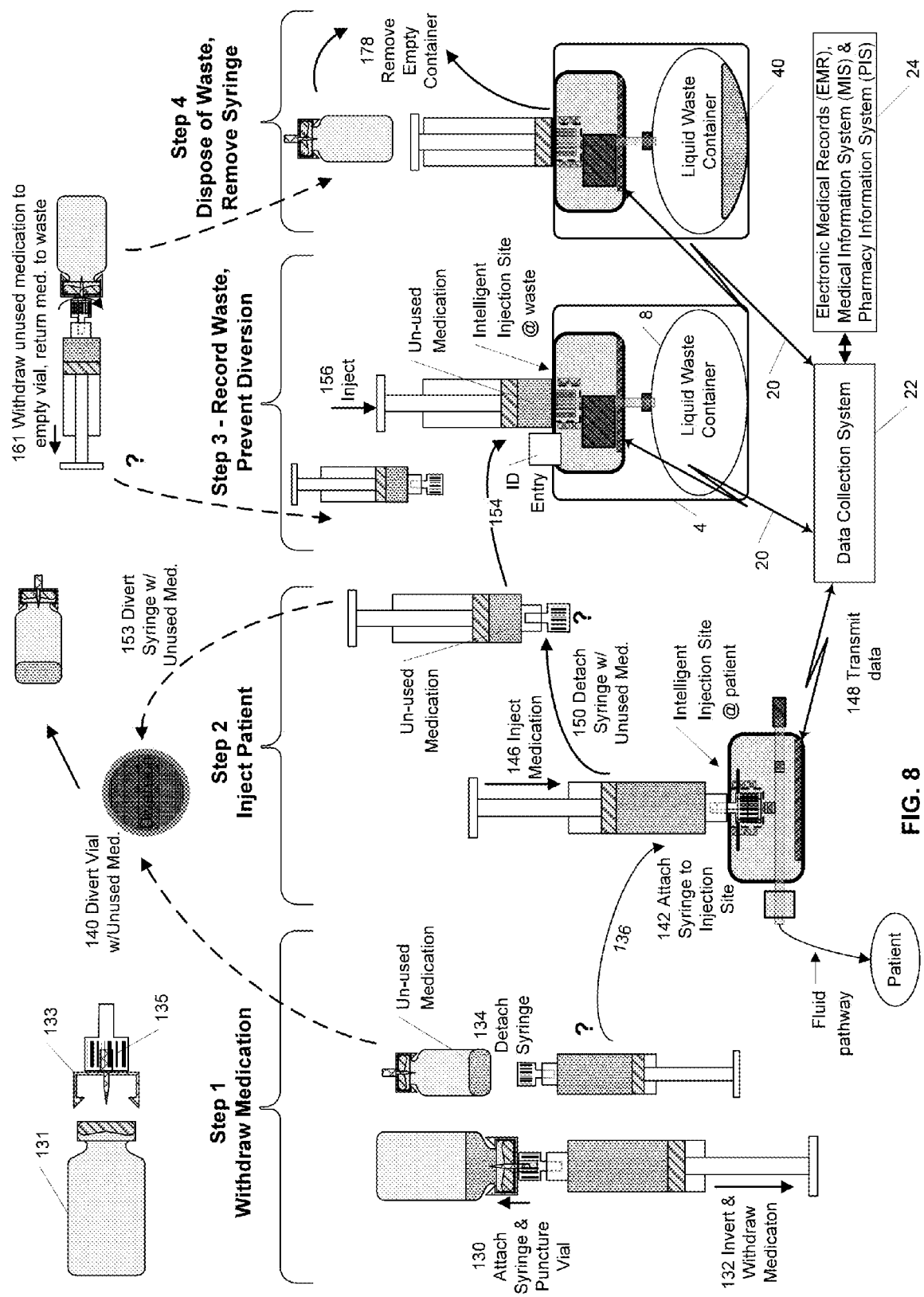
FIG. 8 is a diagram illustrating the sequence of use of a medication waste and data collection system as in FIG. 2 with a vial and medication transfer apparatus.
Figure 9:
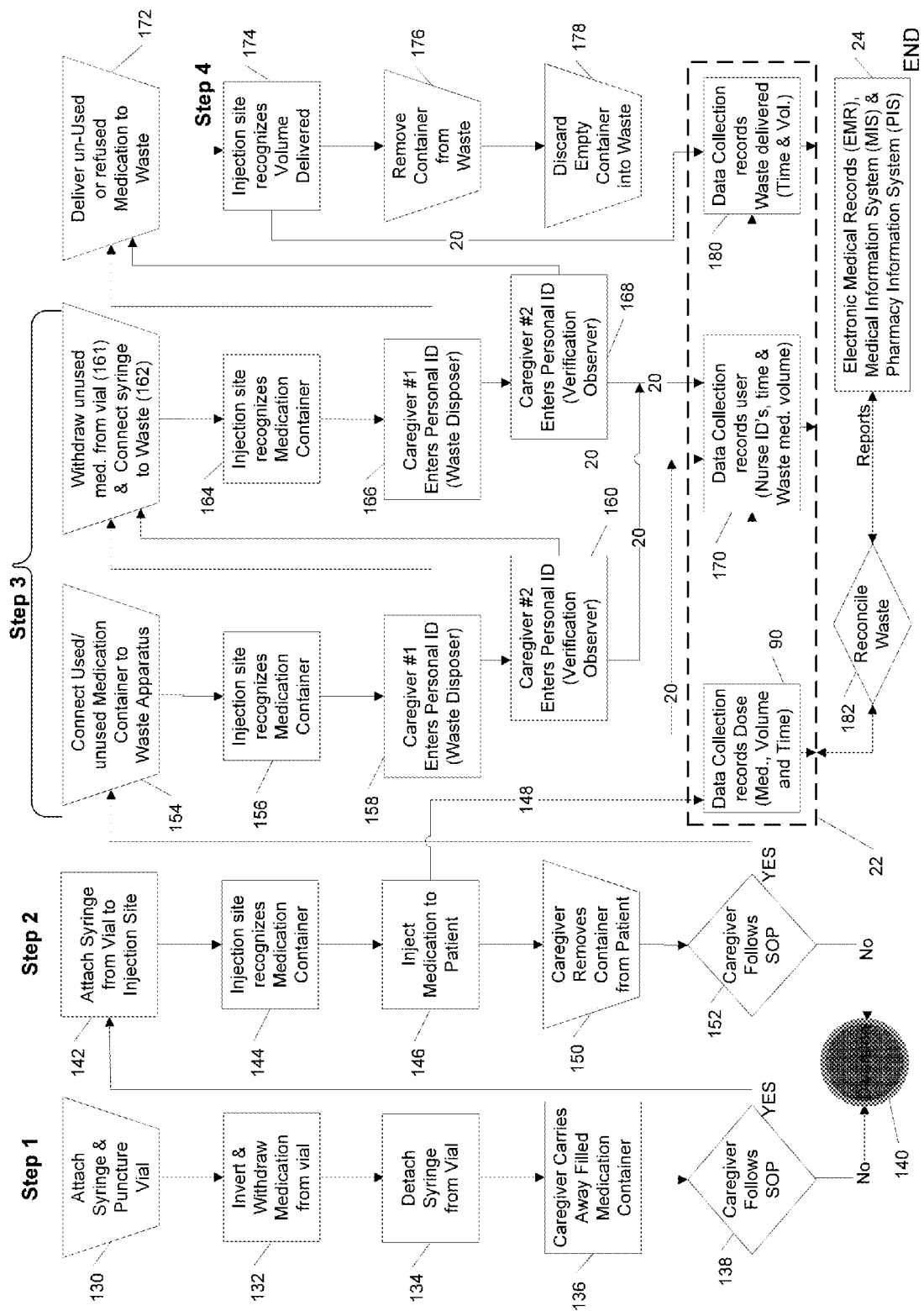
FIG. 9 is a logic flow diagram illustrating the process steps of FIG. 8.

FIGS. 8 and 9 are diagrams illustrating a sequence of use of a medication waste and data collection system as in FIG. 1 with a vial 131 and a medication transfer apparatus 133 with medication ID code 135. Other medication preparation and transfer apparatus 5 can include needles, luer fittings, tubing connectors, etc. for the preparation and transfer of medication from a primary container to a secondary container. Medication dose preparation and transfer can include an apparatus 5 that identifies a primary medication container ID code 13 and a secondary medication container ID code 14 and associates each ID code with the other as described earlier. Medication transfer can occur in a pharmacy, at a medication dispensing station or at a patient care site (a bedside, a care unit in a facility or any care area during emergency or other medical services). The waste disposal step can be before medication administration to a patient (dispose of medication not intended for patient administration first, then administer residual to a patient) or dispose step can be after medication administration to a patient (administer medication to a patient first, then dispose of any residual unused medication). The there are 4 major steps in the process:

Step 1—Withdraw medication from vial; provide third data
Step 2—Inject medication into patient; provide first data
Step 3—Deliver unused medication to a liquid waste container apparatus and record waste; provide second data;
Step 4—Reconcile waste using first, second and/or third data and dispose of empty container.

The following is a more detailed description of the process and moves from left to right. Numbers in parentheses (#) refer to sub-steps as shown in FIGS. 8 and 9. There may be any number of sequences in the administration of medications to patients and the recording of data for these steps. Each sequence would typically follow the basic steps of acquiring medication, administering medication, disposing of unused medication, Alternately, the unused medication portion can be disposed of first and then the remaining dose of medication administered to the patient.

Step 1—Medication is prescribed and a medication vial is accessed from inventory for patient care. A caregiver attaches medication vial 131 to a medication transfer apparatus 133 or medication preparation and transfer apparatus 5 (step 130), inverts and withdraws medication into a syringe (132) and detaches syringe from the vial (134). Third data can be provided to data collection system 22. A caregiver carries away the filled medication container (syringe) (136). The caregiver can follow the SOP and take the filled syringe to the patient (138). Optionally the caregiver can divert the medication container (140).

Step 2—The caregiver attaches the syringe to an intelligent injection site 3 connected to a patient (142). The intelligent injection site 3 recognizes the medication container identification code 135 (step 144). The caregiver injects the medication (146) which is delivered to the patient via a fluid pathway. The volume of medication delivered is measured by the intelligent injection site 3 and first data (148) is time stamped and transmitted to data collection system 22 where medication container identity, medication type, concentration, volume and time is recorded (90). The caregiver then removes the container from the injection site (150) and leaves the patient.

Caregiver carries away medication container (150) and decides how to dispose of unused medication according to SOP (152). If caregiver diverts medication (140), SOP is not followed. If caregiver follows SOP, unused medication is delivered to a medication waste collection apparatus (154).

Step 3—Caregiver locates the waste disposal system and connects medication container to intelligent injection site 6 at waste collection apparatus (154). Injection site 6 recognizes the medication container ID code (156). Caregiver #1 enters personal ID information into waste disposal system (158). Caregiver #2 enters personal ID information into waste disposal system (160). Medication container ID Code and Caregivers' ID information is transmitted 20 to data collection system 22 where information is recorded (170). Caregiver #1 (or #2) delivers unused medication by injecting medication into injection site. Caregiver #2 (or #1) observes waste process and injection site 6 recognizes the wasted medication volume and transmits medication container identity, medication ID Code, volume injected and time data (second data) to data collection system 22. Data collection system 22 records data (170).

A second liquid waste disposal step, if required for the vial with unused medication, can now be accounted for. The caregiver withdraws the unused medication from the vial with a syringe (161), locates the waste disposal system and connects medication container to intelligent injection site at waste system (162). Injection site recognizes the medication container ID code (164). Caregiver #1 enters personal ID information into waste disposal system (166). Caregiver #2 enters personal ID information into waste disposal system (168). Medication container ID Code and Caregivers' ID information is transmitted (20) to data collection system 22 where information is recorded (170). Caregiver #1 (or #2) delivers unused medication by injecting medication into injection site (172). Caregiver #2 (or #1) observes waste process and injection site recognizes the wasted medication volume (174) and transmits 20 medication container identity, medication ID Code, volume injected and time data (second data) to data collection system 22. Data collection system 22 records data (180).

Step 4—Medication container is removed from waste system (176) and empty containers (syringe and vial) are disposed of in solid waste (178). Data collection 22 (or EMR/MIS/PIS 24) reconciles waste volume (182) using original medication container volume from ID Code minus volume injected into patient (90) with wasted medication volume (170) and credits Caregiver #1 and Caregiver #2 with proper medication disposal (reports).

Figure 10:
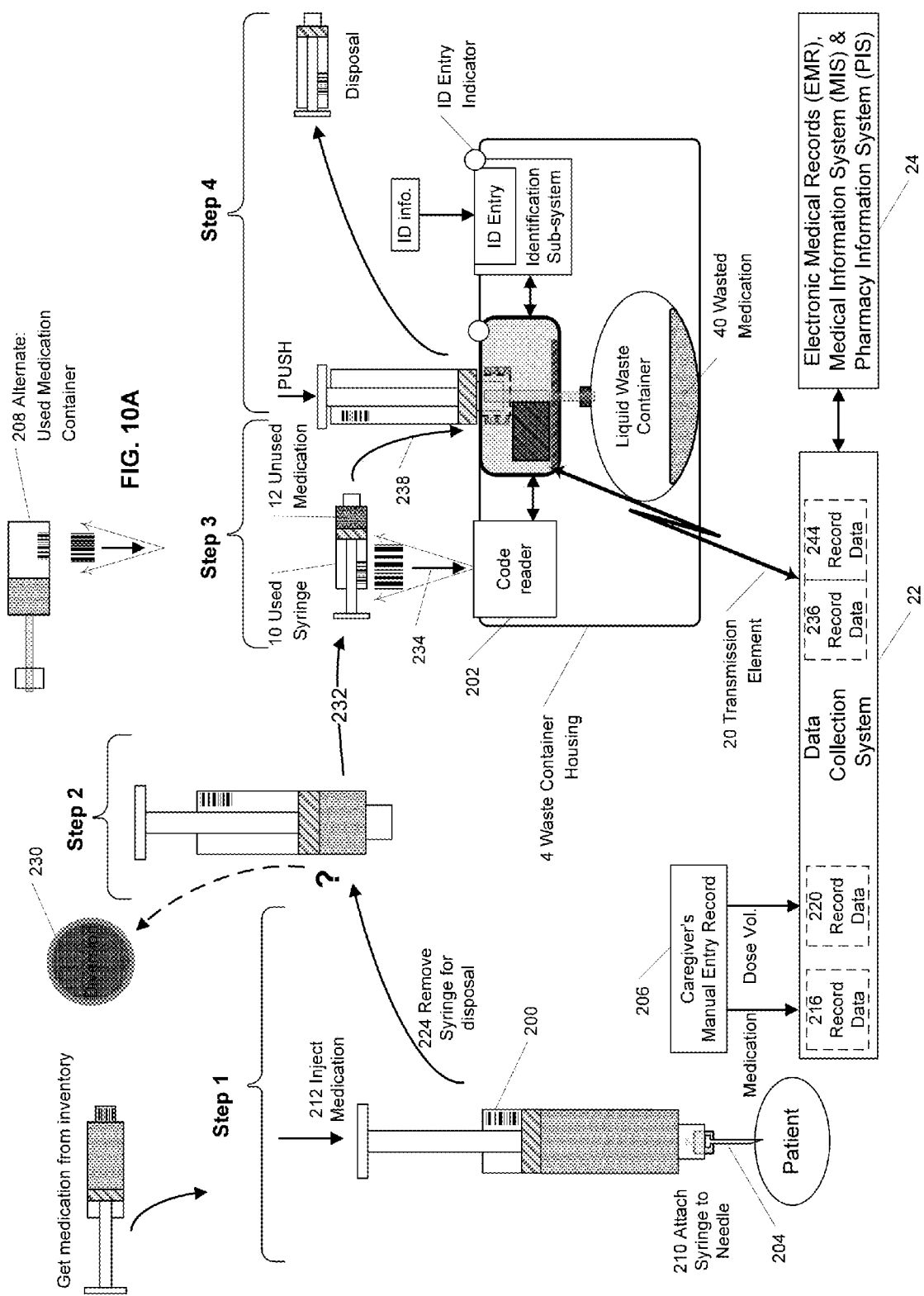
Figure 11:
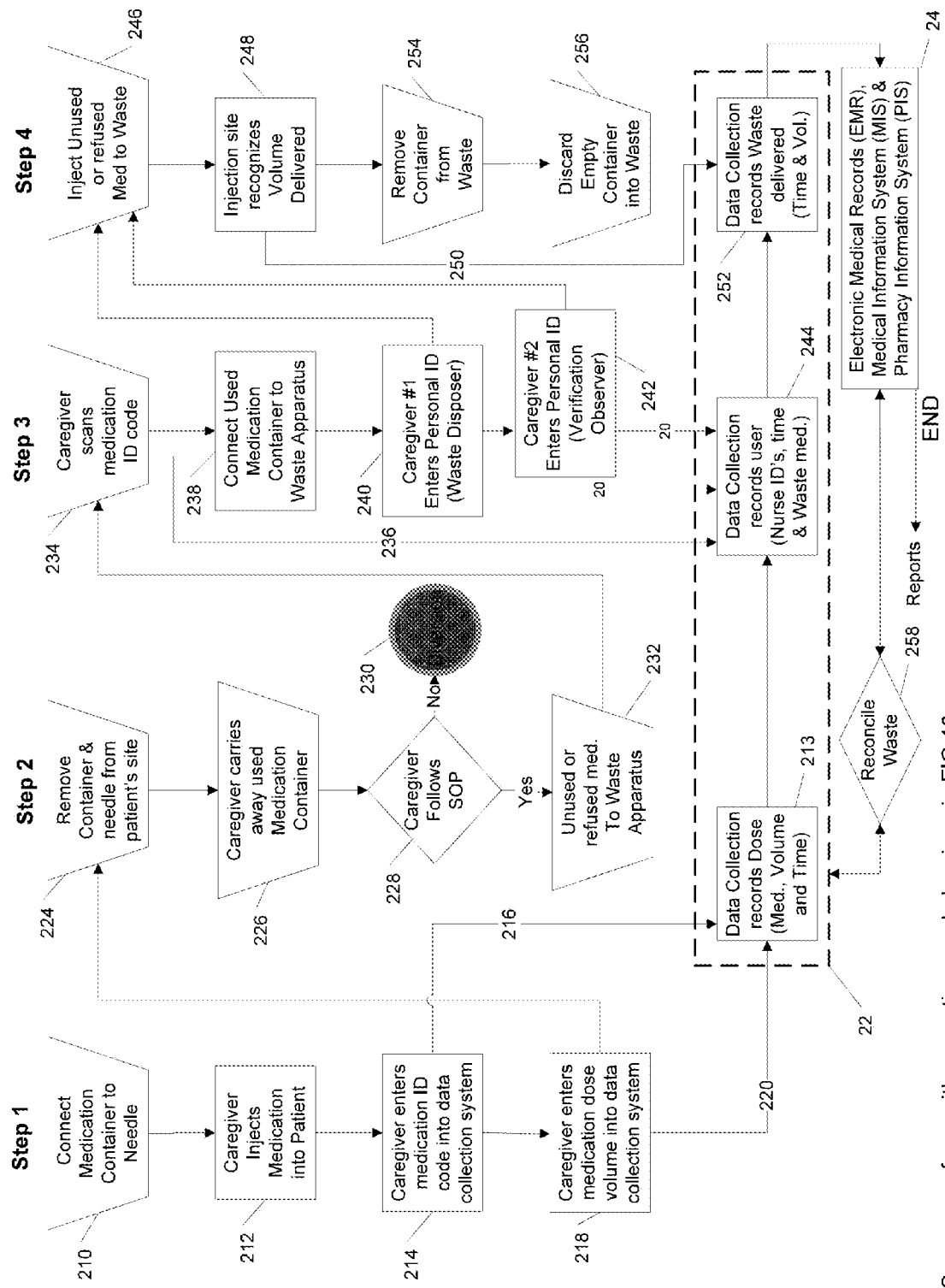
FIG. 11 is a logic flow diagram illustrating the process steps of FIG. 10.

FIGS. 10 and 11 are diagrams illustrating the sequence of use of a medication waste collection apparatus as in FIG. 4. FIG. 11 is a logic flow diagram illustrating the process steps of FIG. 10. In this variation, the medication container has a medication identification ID code (200) on the side of the container instead of at the fluid outlet. Code reader 202 located on the medication waste collection apparatus can read the medication ID code and transmit 20 this information (second data) to a data collection system 22. The medication container can have a needle 204 for direct administration to the patient. The caregiver can use a manual or instrument assisted data entry system 206 to record a medication dose administration. Data entry system 206 can be a stand-alone handheld bar-code medication administration (BCMA) system where the caregiver scans the medication container and a patient's ID (wrist band or similar unique patient identification) to associate the medication administration with the patient. Data entry 206 can be part of a medical device (smart IV pump) at the patient bedside, a drug dispensing system (Pyxis MedStation®) or a medication preparation and transfer system 5. If a partial dose is required, additional data entry may be necessary. Alternately, the medication container can be a rigid or semi-rigid container 208 as shown in FIG. 10A.

The there are 4 major steps in the process shown in FIGS. 10 and 11:

Step 1—Get medication from inventory. Administer medication dose to patient. Record patient's manual dose injection (first data); As an alternative, Step 1 can include the use of a medication preparation and transfer system 5 and produce information (third data) for transmission to data collection system 22.

Step 2—Remove used container from patient's injection site and deliver any unused medication to waste disposal system;

Step 3—Deliver unused medication to a liquid waste collection apparatus and record waste (second data).

Step 4—Reconcile waste and dispose of empty container.

The following is a more detailed description of the process and moves from left to right. Numbers in parentheses (#) refer to sub-steps as shown in FIGS. 10 and 11. There may be any number of sequences in the administration of medications to patients and the recording of data for these steps. Each sequence would typically follow the basic steps of acquiring medication, administering medication, disposing of unused medication, Alternately, the unused medication portion can be disposed of first and then the remaining dose of medication administered to the patient.

Step 1—Medication is prescribed and a full medication container is accessed from inventory for patient care. A caregiver (usually a nurse, but can be any caregiver) attaches medication container to a needle or catheter (210) for injection to a patient. The caregiver injects medication into the patient (212). The caregiver manually enters the medication container identification code into the data collection system (214) and the information is recorded (216). The caregiver manually enters the medication dose volume into the data collection system (218). Alternately, data entry method 206 can include a bar code medication administration (BCMA). A BCMA system can be a standalone system or be part of a medical device like a smart IV pump. Data entry can include caregiver ID, patient ID, medication ID code, dose volume, etc. The volume of medication delivered is time stamped and transmitted (220) to data collection system 22 (first data) where medication container identity, medication type, concentration volume and time is recorded (213).

Step 2—The caregiver removes the container from the injection site (224). Caregiver carries away medication container (226) and decides how to dispose of unused medication according to SOP (228). If caregiver diverts medication (230), SOP is not followed. If caregiver follows SOP, unused medication is delivered to a medication waste collection apparatus system (232).

Step 3—Caregiver locates the medication waste collection apparatus and scans the code 200 of used medication container with code reader 202 (234). Code information 236 is transmitted 20 to data collection system 22 and medication type and concentration information 236 is recorded. The caregiver then connects medication container to the medication waste collection apparatus (238). Caregiver #1 enters personal ID information into waste disposal system (240). Caregiver #2 enters personal ID information into waste disposal system (242). Caregivers' ID information is transmitted (20) to data collection system 22 where information is recorded (244).

Step 4—Caregiver #1 (or #2) delivers unused medication by injecting medication into injection site (246). Caregiver #2 (or #1) observes waste process and injection site recognizes the wasted medication volume (248) and transmits medication volume injected and time data (second data) to data collection system 22 (250). Data collection system 22 records data (252). Medication container is removed from waste system (254) and empty container is disposed of in solid waste (256). Data collection 22 (or EMR/MIS/PIS 24) reconciles waste volume (258) using original medication container volume minus volume injected into patient (220) with wasted medication volume (252) and credits Caregiver #1 and Caregiver #2 with proper medication disposal (reports).

Other variations of medication waste collection apparatus and medication containers can be implemented using various forms of medication information ID code source 14 to provide information about the medication container, the contents of the container and different fluid outlet configurations.

Figure 12:
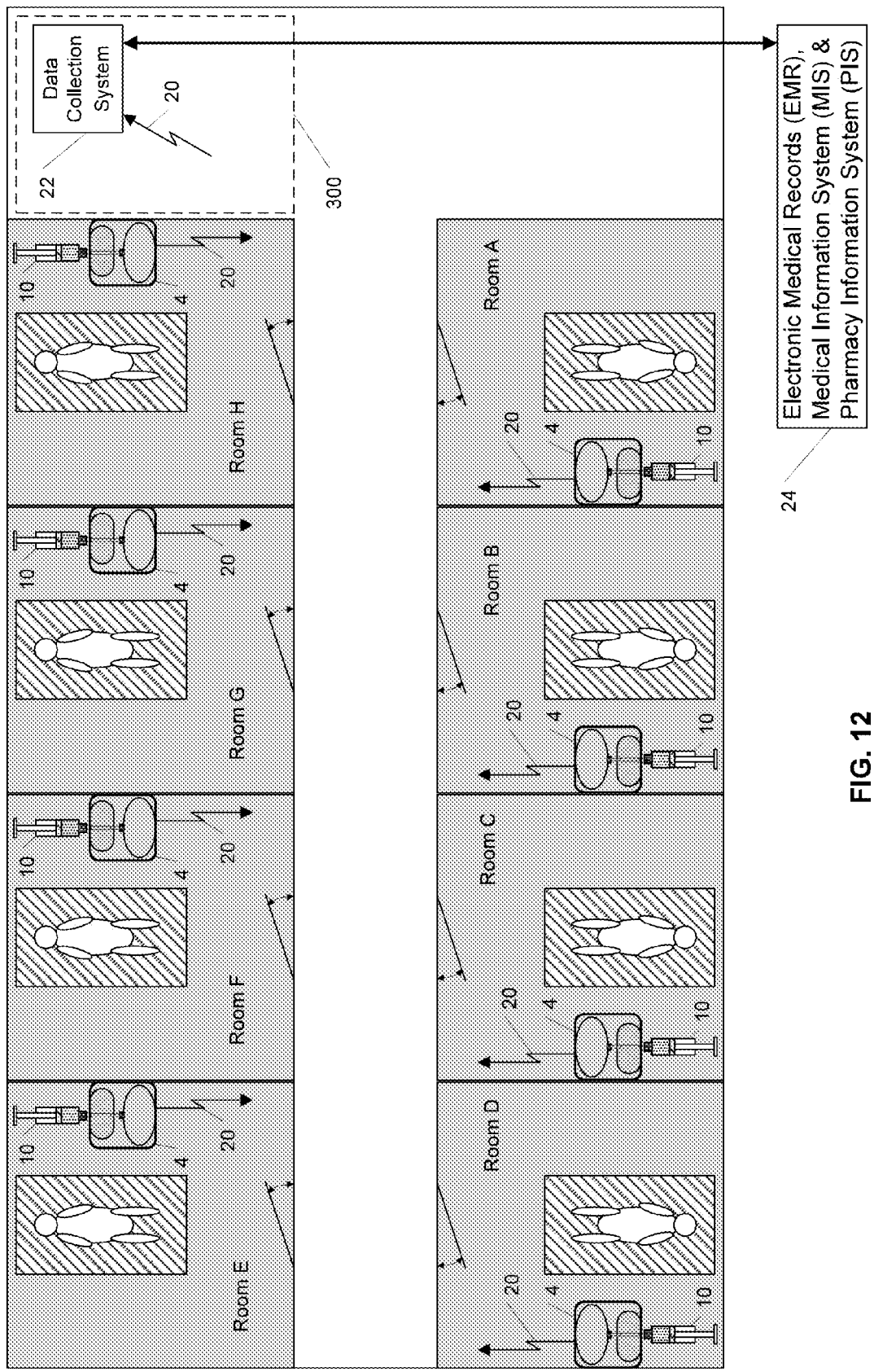
FIG. 12 is a diagram of a facility with multiple medication waste collection apparatus.

FIG. 12 is a diagram of a facility with multiple medication waste collection apparatus in a distributed configuration. Each room (A-H) can be equipped with a medication waste collection housing 4 as part of the medication waste collection apparatus and data collection system. The caregiver can immediately dispose of unused medication 10 in the patient's room and data transmission 20 can be sent immediately to data collection system 22 located at centralized station 300. Alternately, the data (second data) can be stored locally in memory 6b (not shown) and transmitted later to data collection system 22. Electronic Medical Records (EMR), Medical Information System (MIS) & Pharmacy Information System (PIS) 24 can be connected to data collection system 22. Medication waste disposed of in any number of rooms can be tracked and reported by centralized data collection system 22 and medical records system (EMR/MIS/PIS) 24. Reconciliation reports, error messages and transaction histories provide information to a caregiver's supervision to minimize medication diversion. Controlled substances can be better tracked and accounted for.

Another variation of a distributed waste collection system as in FIG. 12 can be for mobile caregivers and EMS vehicles (not shown). Here, waste collection housings 4 can be installed in multiple EMS vehicles and data collection system 22 can be located at a centralized EMS station like a firehouse or ambulance sub-station. Clock 6a and memory 6b within waste collection housing 4 (shown in FIG. 2) can keep a time stamped history log of medication disposal while the EMS vehicle is out in the field and then upon return to central station 300 data transmission 20 can be completed and a historical log received by data collection 22. Reconciliation reports, error messages and transaction histories can provide information to a caregiver's supervision to minimize medication diversion. Controlled substances can be better tracked and accounted for.

Figure 13:
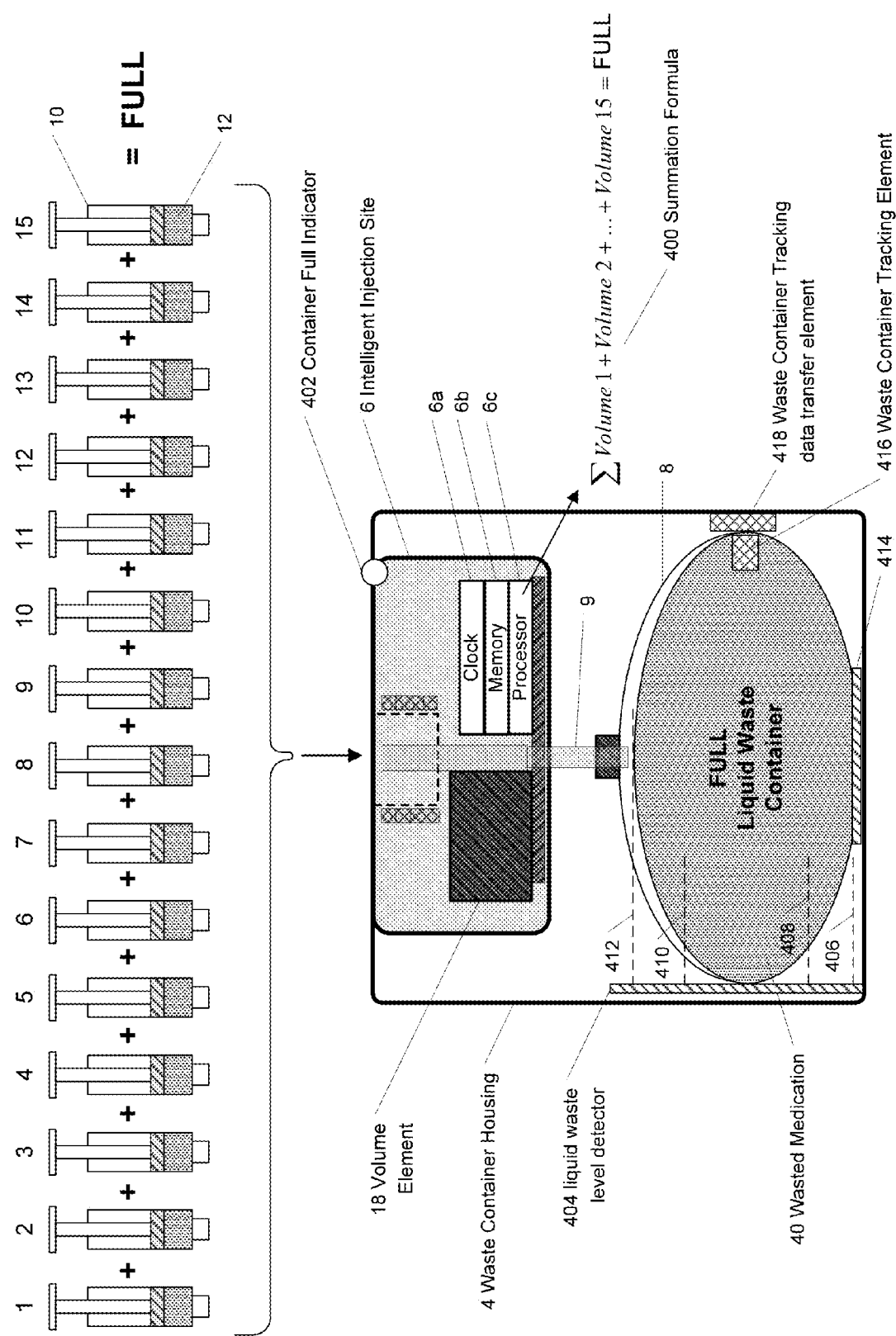
FIG. 13 is a diagram illustrating a volume accumulator and tracking element for a medication waste collection apparatus as in FIG. 2.

FIG. 13 is a diagram illustrating a liquid waste volume accumulator and tracking element for a medication waste collection apparatus and data collection system as in FIG. 2. Multiple used medication containers 10 can dispose of unused medication 12 in a single waste container housing 4. Each disposed volume (Volume 1 from container 1, Volume 2 from container 2, etc.) can be can be summed by processor 6c as represented in formula 400. When the sum of disposed volumes equals the maximum capacity of liquid waste container 8 a container FULL indicator 402 can be activated to indicate that replacement of the liquid waste container 8 is necessary. The entire waste container housing 4 can be replaced or optionally only the full liquid waste container 8.

A second variation of a liquid waste volume accumulator can be a liquid waste level detector 404. Liquid level detector 404 can be any of a float detector, an ultrasonic fluid level detector, a strain gage weight detector, an optical fluid level detector, a conductive level detector, a resistive level detector, a maximum limit switch activated by a float or any one of a number of level detector means. Initially, when the liquid waste container is empty, empty level 406 is detected indicating the liquid waste container 8 is properly installed in waste container housing 4. As liquid waste accumulates level detector 404 can indicate the amount of liquid waste accumulated. As the fluid waste accumulates any number of level indications can be made including, but not limited to approximately ¼ full (408), and later approximately ¾ full (410) and even later approximately full (412).

As a third variation of a liquid waste volume accumulator, volume detector 414 can be included that detects liquid waste as it accumulates and detects a volume level for each residual medication disposal. Here, the previous volume detected is subtracted from the new volume detection to give the net volume disposed of residual medication. Liquid waste volume detector 414 can be a strain gage sensor/detector, an ultrasonic volume detector, an optical volume detector or any one of a number of other volume detection means.

The liquid waste container 8 can include a waste container tracking element 416. The tracking element 416 can be utilized to identify the waste contents as hazardous, non-hazardous, information regarding the dates, times, volumes and medication types and concentrations disposed of in the liquid waste container. The tracking element 416 can be serialized for tracking of safe and proper waste disposal when the liquid waste container is removed from waste collection housing 4. Waste container housing 4 can include a waste container data transfer element 418. Waste container data transfer element 418 can transfer tracking information from the liquid waste collection apparatus 2 to the tracking element 416. The tracking information can include medication disposal dates, times, volumes, medication types, medication concentrations, liquid waste container serial numbers. Waste container tracking element 416 can be an RFID tag, an electronic data chip, a magnetic strip with encoded information. Waste container data transfer element 418 can be an RFID reader/writer, an electronic data chip reader/writer, a magnetic strip reader/writer.

FIG. 14 is a table of examples of possible medication waste disposal rules. These rules are examples and are not intended to be the only possible rules. Many combinations and rule limits of the various recorded data can be established and programmed into the medication waste collection apparatus and/or data collection system. When rules are not met various indicators can be activated, various alert and/or warning messages can be sent to caregivers and/or caregiver supervisors and various reports can be completed. Rules can be customized for each system installation and can be changed as SOP's are changed. Rules can be incorporated that apply to specific classes of input data. For example, there can be dedicated rules for specific medication types, categories of medications, clinician ID profiles (nurses, nurse managers, physicians), individual clinician IDs on a diversion watch list, container types, and other input variables detectable by a medication waste and data collection system. Standardized rules and reports can be pre-programmed and customizable fields (times, volumes, ID numbers, applicable medications, etc.) can be provided to adjust rules to local installation preferences.

The rules described in FIG. 14 can be implemented within the waste container housing 4's processor 6c, within data collection system 22, in the institution's/agency's centralized EMR/MIS/PIS system 24 or in any combination of the above. The alerts and/or warnings can be stored in memory 6b, in data collection system 22 or EMR/MIS/PIS system 24 for immediate and/or periodic reporting. Reports, alerts and/or warnings about potential medication diversion can be sent to central station computer systems, supervisor's cellular phones and many other types of electronic data systems and/or displays.

In a second aspect, rules can be included to provide a safety check on the volume of medication dosed to the patient. Patient dose volumes (first data) can be subtracted from initial medication container volumes (third data) and compared to actual waste disposal volumes (second data). If there is a difference an alert, alarm or warning message can be sent or included in a report (immediate report, shift report, daily report, weekly report, patient record report, medication reconciliation report, supervisor report, caregiver report, a pharmacy report, etc.). Other rules can be applied before medication administration to the patient in that an unused medication volume can be first disposed of into the medication waste collection apparatus (second data) and then secondly the remaining volume of medication in the container can be administered to the patient (first data). Amounts disposed can be subtracted from the initial medication container volume and the residual volume would then be injected into the patient (first data). A rule can be constructed to check the difference in the patient administered medication volume from the residual volume is the same thus indicating the absence of medication diversion. A lower than expected patient administration volume (short shot administration) could indicate a diverted medication and/or an under medication administration to the patient. A violation of the rule can result in an alert, alarm, warning message or report.

While the foregoing systems and techniques are mainly described as using a medication container with identification information (which in turn is read/scanned), it will be appreciated that other techniques can be used at any of the medication preparation, medication administration, and medication disposal steps to characterize the medication. For example, the waste collection system can incorporate a composition sensor to generate, for example, a spectroscopic signature of the medication and compare it to known (i.e., empirically derived, etc.) spectroscopic signatures in order to characterize the medication within the container. Such a composition sensor can replace the scanning of the medication identification information or alternatively it can act as a secondary check regarding the medication. Stated differently, the waste collection system can scan the medication container and additionally perform composition analysis (e.g., spectroscopic analysis, etc.) in order to verify the medication being wasted. The medication preparation and transfer system 5 and the medication injection site 3 can also include a composition sensor in order to characterize the contents of the medication container (and such composition information can replace or supplement medication identification information applied or otherwise associated with the medication container). In such cases, data generated by one or both of the medication preparation and transfer system 5 and the medication injection site 3 can be compared with the data generated by the waste collection system in order to determine whether any medication in the medication container 10 has been diverted.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Aspects of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and an input interface such as a touch screen, keyboard and a pointing device (e.g., a mouse or a trackball) by which the user may provide input to the computer. Other kinds of devices such as cellular phones, smart phones, IPADs, tablet PC's and medical devices including but limited to smart IV pumps may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

In addition, aspects of the subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet. Communications and transmissions can be wired or wireless or combinations of wired and wireless communications.

Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows and steps for use described herein do not require the particular order shown, or sequential order, to achieve desirable results. Other embodiments can be within the scope of the following claims.

What is claimed is:

1. A system comprising:
a remote data collection system comprising at least one computing system;
a medication injection site to characterize administration of medication to a patient, the medication site comprising:
a first housing,
a fluid conduit at least partially extending within the first housing and configured to deliver medication within a medication container to a patient;
a medication port extending from an external surface of the first housing configured to be coupled to a fluid outlet of the medication container, the medication port being fluidically and directly coupled to the fluid conduit,
at least one first sensor disposed within the first housing to generate data characterizing administration of the medication,
a first transmitter within the first housing to wirelessly transmit data generated by the sensor to the remote data collection system, and
a self-contained power source within the first housing powering the at least one first sensor and the first transmitter;
and
a waste collection system to receive unused medication within the medication container for disposal, the waste collection system comprising:
a second housing,
an inlet port extending from an external surface of the second housing configured to be coupled to the fluid outlet of the medication container,
at least one second sensor disposed within the second housing, the at least one second sensor, solely upon coupling of the fluid outlet of the medication container to the inlet port, generating data to identify medication received by the at least one waste collection system,
at least one third sensor disposed within the second housing for measuring a volume of medication received by the at least one waste collection system and generating data specifying the measured volume, and
a second transmitter for wirelessly transmitting the data from the at least one second sensor and the at least one third sensor to the remote data collection system to characterize wasted medication in the medication container.

2. A system as in claim 1, wherein the remote data collection system determines whether medication within the medication container has been diverted based on the received data uses a rules set defining parameters indicative of medication diversion to determine whether medication within the medication container has been diverted.

3. A system as in claim 2, further comprising:
a dispensing station to dispense the medication container and to generate dispensing data identifying the medication container identity, medication and concentration, an amount of medication initially in the medication container, the dispensing system being in communication with the remote data collection system;
wherein the remote data collection system further determines whether medication within the medication container has been diverted based on the dispensing station data.

4. A system as in claim 2, further comprising:
a medication preparation system to prepare the medication container prior to administration of the medication to the patient, the medication preparation system generating medication preparation data identifying the medication container identity, medication and concentration, an amount of medication initially in the medication container, the medication preparation system being in communication with the remote data collection system;
wherein the remote data collection system further determines whether medication within the medication container has been diverted based on the medication preparation data.

5. A system as in claim 4, wherein the medication preparation data is identified when a fluid outlet of the medication container is coupled to a fluid inlet of the medication preparation system and medication is transferred from a medication source to the medication container through a portion of the medication preparation system.

6. A system as in any claim 4, wherein the data collection system provides an expected medication volume to the medication injection site based on the data generated by the at least one second sensor and/or the medication preparation data.

7. A system as in claim 6, wherein the data generated by the at least one first sensor is compared to the data generated by the at least one second sensor and/or the medication preparation data to determine if a complete administration of medication was injected to the patient.

8. A system as in claim 7, wherein the data collection system generates a message or alert when the comparison indicates an incomplete administration of medication to a patient.

9. A system as in claim 1, wherein the medication container bears an information element disposed on a portion of the medication container that is on a tip portion of the fluid outlet and characterizing the contained medication.

10. A system as in claim 1, wherein the medication container bears an information element indicative of an identity of the medication container.

11. A system as in claim 10, wherein the information element is a barcode, an optical code, an RFID tag, a magnetic code, a data chip, or other data storage media.

12. A system as in claim 1, wherein the medication container bears an information element characterizing the contained medication and an information element indicative of an identity of the medication container.

13. A system as in claim 1, wherein the remote data collection system logs the received data.

14. A system as in claim 1, wherein the remote data collection system is coupled to one or more external sources selected from a group consisting of a: electronic medical records (EMR) system, a medical information systems (MIS), and a pharmacy information system (PIS) 24.

15. A system as in claim 14, wherein data received by the external source is used by the remote data collection system to determine whether any medication has been diverted.

16. A system as in claim 1, wherein the remote data collection system applies a rules set to determine characteristics associated with administration and wasting of the medication in the medication container based on the transmitted data.

17. A fluid handling system for receiving a medication container having a fluid outlet and for reporting information to a data collection system comprising:
a medication injection site comprising:
a first housing,
a fluid conduit at least partially extending within the first housing and configured to deliver medication within a medication container to a patient;
a medication port extending from an external surface of the first housing configured to be coupled to a fluid outlet of the medication container, the medication port being fluidically and directly coupled to the fluid conduit,
at least one first sensor disposed within the first housing to generate data characterizing administration of the medication,
a first transmitter within the first housing to wirelessly transmit data generated by the sensor to the remote data collection system, and
a self-contained power source within the first housing powering the at least one first sensor and the first transmitter; and
a liquid waste injection site comprising:
a second fluid inlet configured to receive the fluid outlet of the medication container;
a third sensor configured to read the identifying information solely in response to the fluid outlet of the medication container being coupled to the second fluid inlet;
a fourth sensor comprising at least one flow sensor configured to generate disposed volume information indicative of an amount of medication injected into the waste injection site; and
a second transmitter configured to transmit the identifying and disposed volume information to the data collection system.

18. The fluid handling system of claim 17 further comprising a medication preparation apparatus comprising:
a fluid coupler configured to transfer medication from a vial to the medication container;
a fifth sensor configured to read the identifying information;

a sixth sensor configured to generation transferred volume information indicative of an amount of medication transferred from the vial to the medication container; and a third transmitter configured to transmit the identifying and transferred volume information to the data collection system.

19. A system comprising:

a medication injection site for receiving a medication container having a fluid outlet and for reporting information to a data collection system; and a waste injection site comprising:
- a first housing;
- a waste containment reservoir within the housing;
- a fluid inlet coupled to the waste containment reservoir extending outwards from the housing and configured to receive the fluid outlet;
- a first sensor disposed within the housing that is configured to automatically read identifying information from the medication container solely in response to the fluid inlet being coupled to the fluid outlet;
- a second sensor disposed within the housing comprising a flow sensor configured to measure a volume of fluid transferred from the medication container to the waste containment reservoir; and
- a first transmitter disposed within the housing that is configured to wirelessly transmit the information indicative of the identifying information and the volume of fluid obtained by the first sensor and the second sensor to the data collection system.

wherein the medication injection site comprises:
- a second housing,
- a fluid conduit at least partially extending within the second housing and configured to deliver medication within the medication container to a patient;
- a medication port extending from an external surface of the second housing configured to be coupled to a fluid outlet of the medication container, the medication port being fluidically and directly coupled to the fluid conduit,
- at least one third sensor disposed within the second housing to generate data characterizing administration of the medication,
- a second transmitter within the first housing to wirelessly transmit data generated by the at least one third sensor to the remote data collection system, and
- a self-contained power source within the first housing powering the at least one third sensor and the second transmitter.

20. A system comprising:

at least one data collection system comprising at least one computing system;

a plurality of medication injection sites, each medication injection site characterizing administration of medication to a patient and comprising at least one first sensor to generate first data to identify and quantify medication administered to the patient and to identify a medication container housing the medication, each medication injection site comprising: a first housing, a fluid conduit at least partially extending within the first housing and configured to deliver medication within a medication container to a patient; a medication port extending from an external surface of the first housing configured to be coupled to a fluid outlet of the medication container; and a plurality of waste collection systems to each receive unused medication within the medication containers for disposal, each waste collection system comprising at least one second sensor comprising a flow sensor to generate second data to identify and quantify medication received by the at least one waste collection system and at least one third sensor generate third data to identify medication containers housing the medication solely when the medication containers are being coupled to the waste collection system, each waste collection system transmitting the second data from the at least one second sensor and the third data from the at least one third sensor to the at least one data collection system;

wherein the at least one data collection system determines whether medication within the medication container has been diverted based on the received first, second, and third data.

21. A system as in claim 20, further comprising:

a plurality of medication preparation systems to each prepare medication containers prior to administration of the medication to the patient, each medication preparation system generating fourth data identifying the medication and an amount of medication initially in the medication container, the medication preparation system being in communication with the at least one data collection system;

wherein the at least one data collection system further determines whether medication within the medication container has been diverted based on the fourth data.

22. A system as in claim 20, wherein the first sensor generates the first data in response to the medication container being coupled to a corresponding medication injection site.

23. A system comprising:

a medication injection site to automatically characterize medication administered to a patient from a medication container;

a waste collection system to receive unused medication within the medication container and to automatically characterize the received unused medication by measuring a volume of fluid expelled from the medication container and by detecting an optical identifier on the medication container solely and automatically as the medication container is being coupled to the waste collection system;

a data collection system receiving data from each of the medication injection site and the waste collection system to determine whether medication has been diverted subsequent to the administration of medication to the patient;

wherein at least one of the medication injection site and the waste collection system uses a composition sensor to characterize a composition of the medication.

wherein the medication injection site comprises
- a first housing,
- a fluid conduit at least partially extending within the first housing and configured to deliver medication within the medication container to the patient,
- a medication port extending from an external surface of the first housing configured to be coupled to a fluid outlet of the medication container, the medication port being fluidically and directly coupled to the fluid conduit,
- at least one first sensor disposed within the first housing to generate data characterizing administration of the medication,
- a transmitter within the first housing to wirelessly transmit data generated by the sensor to the remote data collection system, and a self-contained power source within the first housing powering the at least one first sensor and the transmitter.

\* \* \* \* \*